(12) United States Patent
Goetsch

(10) Patent No.: US 8,623,359 B2
(45) Date of Patent: Jan. 7, 2014

(54) COMBINATION OF A C-MET ANTAGONIST AND AN AMINOHETEROARYL COMPOUND FOR THE TREATMENT OF CANCER

(75) Inventor: Liliane Goetsch, Ayze (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 98 days.

(21) Appl. No.: 13/002,875

(22) PCT Filed: Jul. 8, 2009

(86) PCT No.: PCT/EP2009/058709
§ 371 (c)(1),
(2), (4) Date: Jan. 6, 2011

(87) PCT Pub. No.: WO2010/003992
PCT Pub. Date: Jan. 14, 2010

(65) Prior Publication Data
US 2011/0117098 A1  May 19, 2011

Related U.S. Application Data

(60) Provisional application No. 61/129,598, filed on Jul. 8, 2008.

(30) Foreign Application Priority Data

Jul. 8, 2008  (EP) .................................. 08305387

(51) Int. Cl.
*A61K 39/395* (2006.01)

(52) U.S. Cl.
USPC ........................................................ 424/133.1

(58) Field of Classification Search
None
See application file for complete search history.

(56) References Cited

U.S. PATENT DOCUMENTS

2012/0148607 A1* 6/2012 Hultberg et al. ........... 424/174.1
2012/0156206 A1* 6/2012 Hultberg et al. ........... 424/136.1

FOREIGN PATENT DOCUMENTS

| WO | 96/38557 | * | 12/1996 |
| WO | 2005/016382 | * | 2/2005 |
| WO | 2006/021884 | * | 3/2006 |
| WO | 2007/066187 | * | 6/2007 |

* cited by examiner

*Primary Examiner* — Sheela J Huff
(74) *Attorney, Agent, or Firm* — Finnegan, Henderson, Farabow, Garrett & Dunner, L.L.P.

(57) ABSTRACT

The invention also relates to a composition comprising an antibody antagonist to c-Met and an aminoheteroaryl compound, particularly as a medicament. The present invention also comprises a pharmaceutical composition comprising said anti c-Met antibody and said aminoheteroaryl compound as combination products for simultaneous, separate or sequential use. The invention relates to the use of the composition of the invention for the treatment of cancer in a mammal.

Figure 1:
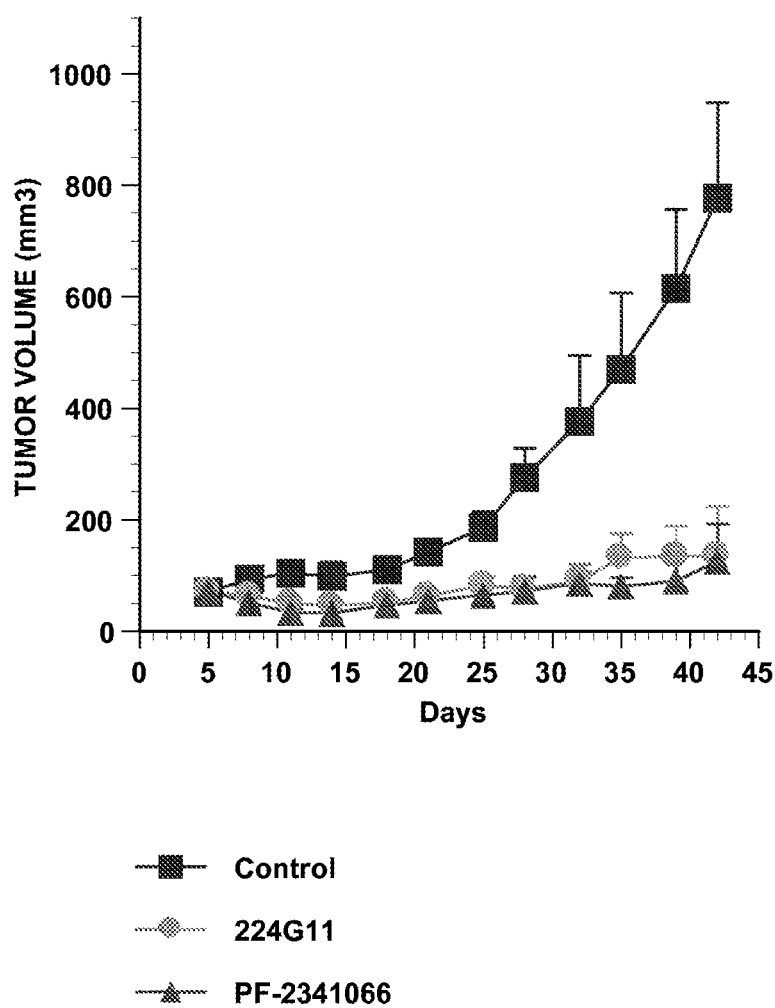

17 Claims, 2 Drawing Sheets

COMBINATION OF A C-MET ANTAGONIST AND AN AMINOHETEROARYL COMPOUND FOR THE TREATMENT OF CANCER

CROSS REFERENCE TO RELATED APPLICATIONS

This is a national stage application under 35 U.S.C. §371 of International Application No. PCT/EP2009/058709, filed Jul. 8, 2009, which claims the benefit under 35 U.S.C. §119(e) of U.S. provisional patent application No. 61/129,598, filed Jul. 8, 2008, and the benefit under 35 U.S.C. §365(b) of European Patent Application EP 08305387.6, filed Jul. 8, 2008.

REFERENCE TO SEQUENCE LISTING SUBMITTED ELECTRONICALLY

An official copy of the sequence listing is submitted electronically via EFS-Web as an ASCII formatted sequence listing with a file named "SequenceListing.txt", created on Jan. 4, 2011, and having a size of 20 kilobytes. The sequence listing contained in this ASCII formatted document is part of the specification and is herein incorporated by reference in its entirety.

The invention relates to a composition comprising an antibody antagonist to c-Met and an aminoheteroaryl compound, particularly as a medicament. The present invention also comprises a pharmaceutical composition comprising said anti c-Met antibody and said aminoheteroaryl compound as combination products for simultaneous, separate or sequential use. The invention relates to the use of the composition of the invention for the treatment of cancer in a mammal.

c-Met, is the prototypic member of a sub-family of RTKs which also includes RON and SEA. The c-Met RTK family is structurally different from other RTK families and is the only known high-affinity receptor for hepatocyte growth factor (HGF), also called seater factor (SF) [D. P. Bottaro et al., Science 1991, 251: 802-804; L. Naldini et al., Eur. Mol. Biol. Org. J. 1991, 10:2867-2878]. c-Met and HGF are widely expressed in a variety of tissue and their expression is normally restricted to cells of epithelial and mesenchymal origin respectively [M. F. Di Renzo et al., Oncogene 1991, 6:1997-2003; E. Sonnenberg et al., J. Cell. Biol. 1993, 123:223-235]. They are both required for normal mammalian development and have been shown to be particularly important in cell migration, morphogenic differentiation, and organization of the three-dimensional tubular structures as well as growth and angiogenesis [F. Baldt et al., Nature 1995, 376:768-771; C. Schmidt et al., Nature. 1995:373:699-702; Tsarfaty et al., Science 1994, 263:98-101]. While the controlled regulation of c-Met and HGF have been shown to be important in mammalian development, tissue maintenance and repair [Nagayama T, Nagayama M, Kohara S, Kamiguchi H, Shibuya M, Katoh Y, Itoh J, Shinohara Y., Brain Res. 2004, 5; 999(2): 155-66; Tahara Y, Ido A, Yamamoto S, Miyata Y, Uto H, Hari T, Hayashi K, Tsubouchi H., J Pharmacol Exp Ther. 2003, 307(1):146-51], their dysregulation is implicated in the progression of cancers.

Aberrant signalling driven by inappropriate activation of c-Met is one of the most frequent alteration observed in human cancers and plays a crucial role in tumorigenesis and metastasis [Birchmeier et al., Nat. Rev. Mol. Cell. Biol. 2003, 4:915-925; L. Trusolino and Comoglio P. M., Nat. Rev. Cancer. 2002, 2(4):289-300].

c-Met activation could result from various mechanisms including i) ligand binding, ii) receptor overexpression which leads to spontaneous ligand independent dimerization, or iii) mutations, mainly occurring in the intracellular domain of c-Met, and resulting in increased and persistent phosphorylation of c-Met or in constitutive receptor activation [J. G. Christensen, Burrows J. and Salgia R., Cancer Letters. 2005, 226:1-26].

Activated c-Met recruits signalling effectors to its multidocking site located in the cytoplasm domain, resulting in the activation of several key signalling pathways, including Ras-MAPK, PI3K, Src and Stat3 [Gao C F, Vande Woude G F, Cell Res. 2005, 15(1):49-51; Furge K A, Zhang Y W, Vande Woude G F, Oncogene. 2000, 19(49):5582-9]. These pathways are essential for tumour cell proliferation, invasion and angiogenesis and for evading apoptosis [Furge K A, Zhang Y W, Vande Woude G F, Oncogene, 2000, 19(49):5582-9; Gu H, Neel B G, Trends Cell Biol. 2003 Mar., 13(3):122-30; Fan S, Ma Y X, Wang J A, Yuan R Q, Meng Q, Cao Y, Laterra J J, Goldberg I D, Rosen E M, Oncogene. 2000 Apr. 27, 19(18): 2212-23]. In addition, a unique facet of the c-Met signalling relative to other RTK is its reported interaction with focal adhesion complexes and non kinase binding partners such as $\alpha 6\beta 4$ integrins [Trusolino L, Bertotti A, Comoglio P M, Cell. 2001, 107:643-54], CD44v6 [Van der Voort R, Taher T E, Wielenga V J, Spaargaren M, Prevo R, Smit L, David G, Hartmann G, Gherardi E, Pals S T, J Biol Chem. 1999, 274 (10):6499-506], Plexin B1 or semaphorins [Giordano S, Corso S, Conrotto P, Artigiani S, Gilestro G, Barberis D, Tamagnone L, Comoglio P M, Nat Cell Biol. 2002, 4(9):720-4; Conrotto P, Valdembri D, Corso S, Serini G, Tamagnone L, Comoglio P M, Bussolino F, Giordano S, Blood. 2005, 105 (11):4321-9; Conrotto P, Corso S, Gamberini S, Comoglio P M, Giordano S, Oncogene. 2004, 23:5131-7] which may further add to the complexity of regulation of cell function by this receptor. Finally recent data demonstrate that c-Met could be involved in tumor resistance to gefitinib or erlotinib suggesting that combination of compound targeting both EGFR and c-Met might be of significant interest [Engelman J A at al., Science, 2007, 316:1039-43].

Greater than 20 mutations have been discovered within the c-met RTK [Ma P. C. et al. Cancer and metastasis rev. 2003, 22:309-25]. The majority of these mutations are missense mutations located in the intracellular part of c-Met, within the tyrosine kinase domain and that can impair affinity or binding properties therapeutic compounds targeting this tyrosine kinase domain. In that way, mutations of c-Met can be more or less responsive to therapeutic inhibitions. For example, in preclinical studies of SU11274 (small molecule tyrosine kinase inhibitor against c-Met), certain mutations were distinguished to be sensitive and resistant to the action of this agent [Schmidt L. et al. Nat. Genet. 1997, 16:68-73; Zhuang Z. et al. Nat. Genet. 1998, 20:66-9]. M1268T and H1112Y were sensitive mutations that showed decreased cell growth and motility. Other mutations such as L1213V and Y1248 were found to be resistant to and unaffected by SU11274 [Hahn O. et al. Hematol Oncol Clin N Am. 2005, 19:343-67]. These studies demonstrate the direct impact of specific mutations on treatments targeting c-Met. However, an oligomerization of c-Met, in presence or in absence of the ligand, is required to regulate the binding affinity and the binding kinetics of the kinase toward ATP and tyrosine-containing peptide substrates [Hays J. 1., Watowich S J, Biochemistry. 2004, 43:10570-8].

In the past few years, many different strategies have been developed to attenuate c-Met signalling in cancer cell lines. These strategies include i) neutralizing antibodies against c-Met or HGF/SF [Cao B, Su Y, Oskarsson M, Zhao P, Kort E J, Fisher R J, Wang L M, Vande Woude G F, Proc Natl Acad Sci USA. 2001, 98(13):7443-8; Martens T, Schmidt N O, Eckerich C, Fillbrandt R, Merchant M, Schwall R, Westphal M, Lamszus K, Clin Cancer Res. 2006, 12(20):6144-52] or the use of HGF/SF antagonist NK4 to prevent ligand binding to c-Met [Kuba K, Matsumoto K, Date K, Shimura H, Tanaka M, Nakamura T, Cancer Res., 2000, 60:6737-43], ii) small ATP binding site inhibitors to c-Met that block kinase activity [Christensen J G, Schreck R, Burrows J, Kuruganti P, Chan E, Le P, Chen J, Wang X, Ruslim L, Blake R, Lipson K E, Ramphal J, Do S, Cui J J, Cherrington J M, Mendel D B, Cancer Res. 2003, 63:7345-55], iii) engineered SH2 domain polypeptide that interferes with access to the multidocking site and RNAi or ribozyme that reduce receptor or ligand expression. Most of these approaches display a selective inhibition of c-Met resulting in tumor inhibition and showing that c-Met could be of interest for therapeutic intervention in cancer.

Within the molecules generated for c-Met targeting, some are antibodies.

One of the most extensively described is the anti-c-Met 5D5 antibody generated by Genentech [WO96/38557] which behaves as a potent agonist when added alone in various models and as an antagonist when used as a Fab fragment. Another antibody targeting c-Met is described by Pfizer as an antibody acting "predominantly as c-Met antagonist, and in some instance as a c-Met agonist" [WO 2005/016382].

The inventor has demonstrated that the antibodies antagonists to c-Met, called 224G11, 227H1, 223C4 and 11E1, or functional fragment thereof, described herein and which have been also described in the patent applications EP 07301231.2 filed on Jul. 12, 2007 and U.S. 61/020,639 filed on Jan. 11, 2008, have the property to inhibit the c-Met dimerization and are active in vivo.

It can then be considered the problem to be solved by the invention as being the provision of a concrete, and not only a putative, combination beneficial for the treatment of cancer.

More particularly, it is an object of the invention to provide a novel and unexpected combination able to affect all the factors involved in the c-Met activation as previously described.

In a general aspect, the invention relates to a method of treatment of cancer in a mammal which comprises administering to said mammal a therapeutically effective amount of a combination of active components comprising an antagonist to c-Met and an aminoheteroaryl compound.

In another general aspect, the present invention is directed to a composition comprising an antibody antagonist to c-Met, or a functional fragment thereof, and an aminoheteroaryl compound, preferably for its use as a medicament.

The present invention is further directed to a pharmaceutical composition comprising at least:

i) one antibody antagonist to c-Met, or a functional fragment thereof; and ii) an aminoheteroaryl compound, as combination products for simultaneous, separate or sequential use.

"Simultaneous use" is understood as meaning the administration of the two compounds of the composition according to the invention in a single and identical pharmaceutical form.

"Separate use" is understood as meaning the administration, at the same time, of the two compounds of the composition according to the invention in distinct pharmaceutical forms.

"Sequential use" is understood as meaning the successive administration of the two compounds of the composition according to the invention, each in a distinct pharmaceutical form.

According to the invention, the combination is preferably mixed with an excipient and/or a pharmaceutically acceptable vehicle.

It is also described and claimed a composition according to the invention as a medicament.

In another embodiment, the combination of the invention may be in the form of a kit of parts. The invention therefore includes a product containing an antibody antagonist to c-Met, or one of these functional fragments, and an aminoheteroaryl compound, preferably capable of inhibiting the c-Met protein kinase activity as defined above, as a combined preparation for simultaneous, separate or sequential delivery for the treatment of cancer in a mammal in need thereof. In one embodiment, a product contains an antibody antagonist to c-Met, or a functional fragment thereof, and an aminoheteroaryl compound as defined above as a combined preparation for simultaneous, separate or sequential use in treating a cancer in a mammal in need thereof.

In one embodiment, the invention provides a pharmaceutical pack containing a course of an anti-cancer treatment for one individual mammal, wherein the pack contains (a) at least one unit of an antibody antagonist to c-Met and (b) at least one unit of an aminoheteroaryl compound in unit dosage form.

In a more specific aspect, the invention deals with a method of treatment of cancer in a mammal which comprises administering to said mammal a therapeutically effective amount of the combination of active components according to the present invention comprising an antibody antagonist to c-Met, or functional fragment thereof, and an aminoheteroaryl compound.

In an also more specific aspect, the invention deals with a composition comprising an antibody antagonist to c-Met, or functional fragment thereof, and an aminoheteroaryl according to the present invention for the treatment of cancer, preferably in a mammal, more preferably in human. Said anticancer treatment comprises administering to said mammal a therapeutically effective amount of the composition of the present invention. Preferably, said composition further comprises a pharmaceutical acceptable carrier and/or excipient.

In a preferred embodiment, said aminoheteroaryl compound is capable of inhibiting the c-Met protein kinase, More preferred are aminoheteroaryl compounds having at least 25%, preferably 40%, 50%, 60%, 75% and 85% of the c-Met protein kinase inhibiting activity demonstrated for the aminoheteroaryl compound named PF-02341066 in the same assay procedure conditions (see herein the complete structure of this PF-02341066 compound).

Among the assay procedures which can be used to determine the level of activity of the c-Met protein kinase in presence of said aminoheroaryl compound, we can cite the procedure assay named "HGFR continuous-coupled spectrophotometric assay" described from page 100 in the PCT patent application published under the number WO 2006/021884.

The terms "antibody", "antibodies" or "immunoglobulin" are used interchangeably in the broadest sense and include monoclonal antibodies (e.g., full length or intact monoclonal antibodies), polyclonal antibodies, multivalent antibodies or multispecific antibodies (e.g., bispecific antibodies so long as they exhibit the desired bio logical activity).

More particularly, such molecule consists in a glycoprotein comprising at least two heavy (H) chains and two light (L) chains inter-connected by disulfide bonds. Each heavy chain is comprised of a heavy chain variable region (or domain) (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

They may also include certain antibody functional fragments, as described in greater detail herein, thereof which exhibit the desired binding specificity and affinity, regardless of the source or immunoglobulin type (i.e., IgG, IgE, IgM, IgA, etc.).

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein (Nature, 256:495-497, 1975).

By the expression "antagonist", it must be understood a compound which is capable of directly or indirectly, counteracting, reducing or inhibiting the biological activity of c-Met.

In general, a "therapeutically effective amount" refers to the minimum concentrations or amounts of a compound or of compounds which are effective to prevent, alleviate, reduce or ameliorate symptoms of disease or prolong the survival of the patient being treated. More particularly, in reference to the treatment of cancer, a therapeutically effective amount refers to that amount which has the effect of (1) reducing the size of (or preferably eliminating) the tumor; (2) inhibiting (that is, slowing to some extent, preferably stopping) tumor metastasis; (3) inhibiting to some extent (that is slowing to some extent, preferably stopping) tumor growth; and/or, (4) relieving to some extent (or preferably eliminating) one or more symptoms associated with the cancer.

More particularly, said antibody antagonist to c-Met, or functional fragment thereof, is selected from the group consisting of:

an antibody (derived from the 224G11 antibody), or a functional fragment thereof, comprising a heavy chain containing CDR-H1, CDR-H2 and CDR-H3 comprising respectively the amino acid sequences SEQ ID Nos. 1, 2 and 3; and a light chain containing CDR-L1, CDR-L2 and CDR-L3 comprising respectively the amino acid sequences SEQ ID Nos. 10, 11 and 12;

an antibody (derived from the 227H1 antibody), or a functional fragment thereof, comprising a heavy chain containing CDR-H1, CDR-H2 and CDR-H3 comprising respectively the amino acid sequences SEQ ID Nos. 4, 5 and 6; and a light chain containing CDR-L1, CDR-L2 and CDR-L3 comprising respectively the amino acid sequences SEQ ID Nos. 13, 11 and 14;

an antibody (derived from the 223C4 antibody), comprising a heavy chain containing CDR-H1, CDR-H2 and CDR-H3 comprising respectively the amino acid sequences SEQ ID Nos. 7, 8 and 9; and a light chain containing CDR-L1, CDR-L2 and CDR-L3 comprising respectively the amino acid sequences SEQ ID Nos. 15, 16 and 17; and an antibody (derived from the 11E1 antibody), comprising a heavy chain containing CDR-H1, CDR-H2 and CDR-H3 comprising respectively the amino acid sequences SEQ ID Nos. 47, 48 and 49; and a light chain containing CDR-L1, CDR-L2 and CDR-L3 comprising respectively the amino acid sequences SEQ ID Nos. 50, 51 and 52.

In a more preferred embodiment, said antibody antagonist to c-Met, or functional fragment thereof, is selected from the group consisting of:

an antibody (derived from the 224G11 antibody), or a functional fragment thereof, comprising a heavy chain comprising the amino acid sequence SEQ ID No. 18 and a light chain comprising the amino acid sequence SEQ ID No. 21;

an antibody (derived from the 227H1 antibody), or a functional fragment thereof, comprising a heavy chain comprising the amino acid sequence SEQ ID No. 19 and a light chain comprising the amino acid sequence SEQ ID No. 22;

an antibody (derived from the 223C4 antibody), a heavy chain comprising the amino acid sequence SEQ ID No. 20 and a light chain comprising the amino acid sequence SEQ ID No. 23; and an antibody (derived from the 11E1 antibody), comprising a heavy chain comprising the amino acid sequence SEQ ID No. 53 and a light chain comprising the amino acid sequence SEQ ID No. 54.

In another particular aspect, said antibody antagonist to c-Met, or functional fragment thereof, are recombinant, chimeric or humanized antibody, or fragment thereof, derived from said 224G11, 227H1, 223C4 or 11E1s antibody (derived is intended to designate the antibodies, or fragment thereof, comprising at least the 6 CDRs, or at least the light and heavy chain as defined above for each of these antibodies).

More particularly, in a preferred embodiment, the present invention relates to a method or a composition according to the invention, wherein said antibody antagonist to c-Met is selected from 224G11, 227H1, 223C4 and 11E1. Collection Nationale de Cultures de Microorganisms (Institut Pasteur, Rue du Docteur Roux, Paris, France), All these monoclonal antibodies were secreted by hybridomas deposited at the CNCM on Mar. 14, 2007 under the numbers CNCM 1-3724 (corresponding to 11E1), I-3731 (corresponding to 224G11), 1-3732 (corresponding to 227H1) and on Jul. 6, 2007 under the number 1-3786 (corresponding to 223C4). These hybridomas consist in murine hybridoma resulting in the cellular fusion of immunized mouse splenocytes with a myeloma cell line (Sp20 Ag14).

By CDR regions or CDR(s), it is intended to indicate the hypervariable regions of the heavy and light chains of the immunoglobulins as defined by IMGT.

The IMGT unique numbering has been defined to compare the variable domains whatever the antigen receptor, the chain type, or the species [Lefranc M.-P., Immunology Today 18, 509 (1997); Lefranc M.-P., The Immunologist, 7, 132-136 (1999); Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cysteine 23 (1st-CYS), tryptophan 41 (CONSERVED-TRP), hydrophobic amino acid 89, cysteine 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002); Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

Three heavy chain CDRs and 3 light chain CDRs exist. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

The following table 1 regroups elements concerning the preferred antibodies.

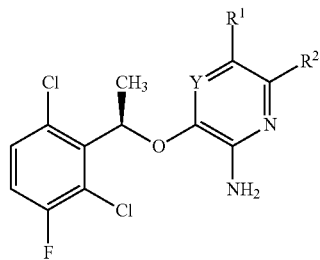

Formula I wherein:

Y is N or $CR^{12}$;

$R^1$ is selected from hydrogen, halogen, $C_{6-12}$ aryl, 5-12 membered heteroaryl, $C_{3-12}$ cycloalkyl, 3-12 membered heteroalicyclic, $-O(CR^6R^7)_nR^4$, $-C(O)R^4$, $-C(O)OR^4$, $-CN$, $-NO^2$, $-S(O)_mR^4$, $-SO_2NR^4R^5$, $-C(O)NR^4R^5$, $-NR^4C(O)R^5$, $-C(=NR^6)NR^4R^5$, $C_{1-8}$ alkyl, $C_{2-8}$ alkenyl, and $C_{2-8}$ alkynyl; and each hydrogen in $R^1$ is optionally substituted by one or more $R^3$ groups;

$R^2$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered het-

TABLE 1

|  | 224G11 I-3731 | | 227H1 I-3732 | | 223C4 I-3786 | | 11E1 I-3724 | |
| --- | --- | --- | --- | --- | --- | --- | --- | --- |
|  | Prot. SEQ ID | Nucl. SEQ ID | Prot; SEQ ID | Nucl. SEQ ID | Prot. SEQ ID | Nucl. SEQ ID | Prot. SEQ ID | Nucl. SEQ ID |
| CDR-H1 | 1 | 24 | 4 | 27 | 7 | 30 | 47 | 55 |
| CDR-H2 | 2 | 25 | 5 | 28 | 8 | 31 | 48 | 56 |
| CDR-H3 | 3 | 26 | 6 | 29 | 9 | 32 | 49 | 57 |
| H. chain | 18 | 41 | 19 | 42 | 20 | 43 | 53 | 61 |
| CDR-L1 | 10 | 33 | 13 | 36 | 15 | 38 | 50 | 58 |
| CDR-L2 | 11 | 34 | 11 | 34 | 16 | 39 | 51 | 59 |
| CDR-L3 | 12 | 35 | 14 | 37 | 17 | 40 | 52 | 60 |
| L. chain | 21 | 44 | 22 | 45 | 23 | 46 | 54 | 62 |

In another preferred embodiment of the method or the composition according to the invention, said antibody antagonist to c-Met is the antibody, or one of these functional fragments, derived from the antibody called 224G11 (comprising at least the 6 CDRs SEQ ID Nos. 1, 2, 3, 10, 11 and 12, or at least the SEQ ID Nos. 18 and 21).

As described in the patent application WO 2006/021884 published on Mar. 2, 2006, (which teaching is incorporated in the present application by reference) aminoheteroaryl compounds are known as c-Met inhibitor and present protein tyrosine kinase activity.

As a surprising result, the applicant of the present application is showing for the first time results illustrating a relevant synergy with the combination of a monoclonal antibody antagonist to c-Met as above described with an aminoheteroaryl compound such as described in the published patent application WO 2006/021884.

The invention concerns a method of, or a composition for the treatment of cancer in a mammal which comprises administering to said mammal a therapeutically effective amount of a combination of active components comprising at least an antibody antagonist to c-Met as above described and an aminoheteroaryl compound, preferably selected from those described in the published patent application WO 2006/021884.

As preferred example, the aminoheteroaryl compound of the composition of the present invention consists in an enantiomerically pure compound of formula I eroalicyclic, 5-12 membered heteroaryl, $-S(O)_mR^4$, $-SO_2NR^4R^5$, $-S(O)_2OR^4$, $-NO_2$, $-NR^4R^5$, $-(CR^6R^7)_nOR^4$, $-CN$, $-C(O)R^4$, $-OC(O)R^4$, $-O(CR^6R^7)_nR^4$, $-NR^4C(O)R^5$, $-(CR^6R^7)_nC(O)OR^4$, $-(CR^6R^7)_nNC^R4R^5$, $-C(=NR^6)NR^4R^5$, $-NR^4C(O)NR^5R^6$, $-NR^4S(O)_pR^5$ or $-C(O)NR^4R^5$, and each hydrogen in $R^2$ is optionally substituted by $R^8$;

each $R^3$ is independently halogen, $C_{1-12}$ alkyl, $C_{2-12}$ alkenyl, $C_{2-12}$ alkynyl, $C_{3-12}$ cycloalkyl, $C_{6-12}$ aryl 3-12 membered heteroalicyclic, 5-12 membered heteroaryl, $-S(O)_mR^4$, $-SO_2NR^4R^5$, $-S(O)2OR^4$, $-NO_2$, $-NR^4R^5$, $-(CR^6R^7)_nOR^4$, $-CN$, $-C(O)R^4$, $-OC(O)R^4$, $-O(CR^6R^7)_nR^4$, $-NR^4C(O)R^5$, $-(CR^6R^7)_nC(O)OR^4$, $-(CR^6R^7)_nOR^4$, $-(CR^6R^7)_nC(O)NR^4R^5$, $-(CR^6R^7)_nNCR^4R^5$, $-C(=NR^6)NR^4R^5$, $-NR^4C(O)NR^5R^6$, $-NR^4S(O)_pR^5$ or $-C(O)NR^4R^5$, each hydrogen in $R^3$ is optionally substituted by $R^8$, and $R^3$ groups on adjacent atoms may combine to form a $C_{6-12}$ aryl, 5-12 membered heteroaryl, $C_{3-12}$ cycloalkyl or 3-12 membered heteroalicyclic group;

each $R^4$, $R^5$, $R^6$ and $R^7$ is independently hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl; or any two of $R^4$, $R^5$, $R^6$ and $R^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of $R^4$, $R^5$, $R^6$ and $R^7$ bound to the same carbon atom may be combined to form a $C_{3-12}$ cycloalkyl, $C_{6-12}$ aryl, 3-12 membered heteroalicyclic or 5-12 membered heteroaryl group; and each hydrogen in $R^4$, $R^5$, $R^6$ and $R^7$ is optionally substituted by $R^8$;

each $R^8$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$NH_2$, —CN, —OH, —O—$C_{1-12}$ alkyl, —O—$(CH_2)_nC_{3-12}$ cycloalkyl, —O—$(CH_2)_nC_{6-12}$ aryl, —O—$(CH_2)_n$(3-12 membered heteroalicyclic) or —O—$(CH2)_n$(5-12 membered heteroaryl); and each hydrogen in $R^8$ is optionally substituted by $R^{11}$;

each $R^9$ and $R^{10}$ is independently hydrogen, halogen, $C_{1-12}$ alkyl, $C_{3-12}$ cycloalkyl, $C_{6-12}$ aryl, 3-12 membered heteroalicyclic, 5-12 membered heteroaryl, —$S(O)_mR^4$, —$SO_2NR^4R^5$, —$S(O)_2OR^4$, —NO2, —$NR^4R^5$, —$(CR^6R^7)_nOR^4$, —CN, —$C(O)R^4$, —$OC(O)R^4$, —$NR^4C(O)R^5$, —$(CR^6R^7)_nC(O)O$ $R^4$, —$(CR^6R^7)_nNCR^4R^5$, —$NR^4C(O)NR^5R^6$, —$NR^4S(O)_pR^5$ or —$C(O)NR^4R^5$; $R^9$ or $R^{10}$ may combine with a ring atom of A or a substituent of A to four a $C_{3-12}$ cycloalkyl, 3-12 membered heteroalicyclic, $C_{6-12}$ aryl or 5-12 membered heteroaryl ring fused to A; and each hydrogen in $R^9$ and $R^{10}$ is optionally substituted by $R^3$;

each $R^{11}$ is independently halogen, $C_{1-12}$ alkyl, $C_{1-12}$ alkoxy, $C_{3-12}$ cycloalkyl, $C_{6-12}$ aryl, 3-12 membered heteroalicyclic, 5-12 membered heteroaryl, —O—$C_{1-12}$, alkyl, —O—$(C_{1-2})_nC_{3-12}$ cycloalkyl, —O—$(CH_2)_nC_{6-12}$ aryl, —O—$(CH_2)_n$(3-12 membered heteroalicyclic), —O—$(CH_2)_n$(5-12 membered heteroaryl) or —CN, and each hydrogen in $R^{11}$ is optionally substituted by halogen, —OH, —CN, —$C_{1-12}$ alkyl which may be partially or fully halogenated, —O—$C_{1-12}$ alkyl which may be partially or fully halogenated, —CO, —SO or —$SO_2$;

$R^{12}$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$S(O)_mR^4$, —$SO_2NR^4R^5$, —$S(O)_2OR^4$, —$NO_2$, —$NR^4R^5$, —$(CR^6R^7)_nC(O)OR^4$, —CN, —$C(O)R^4$, —$OC(O)R^4$, —$O(CR^6R^7)_n$ $R^4$, —$NR^4C(O)R^5$, —$(CR^6R^7)_nC(O)OR^4$, —$(CR^6R^7)_nNCR^4R^5$, —$C(=NR^6)NR^4R^5$, —$NR^4C(O)NR^5R^6$, —$NR^4S(O)_pR^5$ or —$C(O)NR^4R^5$, and each hydrogen in $R^{12}$ is optionally substituted by $R^3$;

each $R^{13}$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$S(O)_mR^4$, —$SO_2NR^4R^5$, —$S(O)_2OR^4$, —$NO_2$, —$NR^4R^5$, —$(CR^6R^7)_nOR^4$, —CN, —$C(O)R^4$, —$OC(O)R^4$, —$O(CR^6R^7)_nR^4$, —$NR^4C(O)R^5$, —$(CR^6R^7)_nC(O)OR^4$, —$(CR^6R^7)_nOR^4$, —$(CR^6R^7)_nC(O)NR^4R^5$, —$(CR^6R^7)_nNCR^4R^5$, —$C(=NR^6)NR^4R^5$, —$NR^4C(O)NR^5R^6$, —$NR^4S(O)_pR^5$, —$C(O)NR^4R^5$, —$(CR^6R^7)_n$(3-12 membered heteroalicyclic), —$(CR^6R^7)_n(C_{3-12}$ cycloalkyl), —$(CR^6R^7)_n(C_{6-12}$ aryl), —$(CR^6R^7)_n$(5-12 membered heteroaryl), —$(CR^6R^7)_nC(O)NR^4R^5$, or —$(CR^6R^7)_nC(O)R^4$, $R^{13}$ groups on adjacent atoms may combine to form a $C_{6-12}$ aryl, 5-12 membered heteroaryl, $C_{3-12}$ cycloalkyl or 3-12 membered heteroalicyclic group, and each hydrogen in $R^{13}$ is optionally substituted by $R^3$;

each m is independently 0, 1 or 2;
each n is independently 0, 1, 2, 3 or 4;
each p is independently 1 or 2;

or a pharmaceutically acceptable salt, hydrate or solvate thereof.

In another preferred example, the said aminoheteroaryl compound consists in an enantiomerically pure compound of formula Ia:

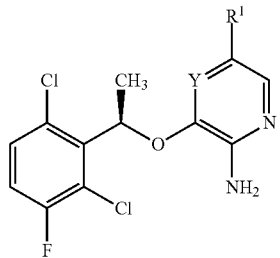

Formula Ia wherein:

Y is N or CH;

$R^1$ is a furan, thiopene, pyrrole, pyrroline, pyrrolidine, dioxolane, oxazole, thiazole, imidazole, imidazoline, imidazolidine, pyrazole pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, trithiane, azitidine or phenyl group; and each hydrogen in $R^1$ is optionally substituted by $R^3$;

each $R^3$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$S(O)_mR^4$, —$SO_2NR^4R^5$, —$S(O)_2OR^4$, —$NO_2$, —$NR^4R^5$, —$(CR^6R^7)_nOR^4$, —CN, —$C(O)R^4$, —$OC(O)_mR^4$, —$O(CR^6R^7)_nR^4$, —$NR^4C(O)R^5$, —$(CR^6R^7)_nC(O)OR^4$, —$(CR^6R^7)_nOR^4$, —$(CR^6R^7)_nC(O)NR^4R^5$, —$(CR^6R^7)_nNCR^4R^5$, —$C(=NR^6)NR^4R^5$, —$NR^4C(O)NR^5R^6$, —$NR^4S(O)_pR^5$ or —$C(O)NR^4R^5$, each hydrogen in $R^3$ is optionally substituted by $R^8$, and $R^3$ groups on adjacent atoms may combine to form a $C_{6-12}$ aryl, 5-12 membered heteroaryl, $C_{3-12}$ cycloalkyl or 3-12 membered heteroalicyclic group;

each $R^4$, $R^5$, $R^6$ and $R^7$ is independently hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl; or any two of $R^4$, $R^5$, $R^6$ and $R^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of $R^4$, $R^1$, $R^6$ and $R^7$ bound to the same carbon atom may be combined to form a $C_{3-12}$ cycloalkyl, $C_{6-12}$ aryl, 3-12 membered heteroalicyclic or 5-12 membered heteroaryl group; and each hydrogen in $R^4$, $R^5$, $R^6$ and $R^7$ is optionally substituted by $R^8$;

each $R^8$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$NH_2$, —CN, —OH, —O—$C_{1-12}$ alkyl, —O—$(CH_2)_nC_{3-12}$ cycloalkyl, —O—$(CH_2)_nC_{6-12}$ aryl, —O—$(CH_2)_n$(3-12 membered heteroalicyclic) or —O—$(CH_2)_n$(5-12 membered heteroaryl); and each hydrogen in $R^8$ is optionally substituted by $R^{11}$;

each $R^9$ and $R^{10}$ is independently hydrogen, halogen, $C_{1-12}$ alkyl, $C_{3-12}$ cycloalkyl, $C_{6-12}$ aryl, 3-12 membered heteroalicyclic, 5-12 membered heteroaryl, —$S(O)_mR^4$, —$SO_2NR^4R^5$, —$S(O)_2OR^4$, —NO2, —$NR^4R^5$, —$(CR^6R^7)_nOR^4$, —CN, —$C(O)R^4$, —$OC(O)R^4$, —$NR^4C(O)R^5$, —$(CR^6R^7)_nC(O)OR^4$, —$(CR^6R^7)_nNCR^4R^5$, —$NR^4C(O)NR^5R^6$, —$NR^4S(O)_pR^5$ or —$C(O)NR^4R^5$; $R^9$ or $R^{10}$ may combine with a ring atom of A or a substituent of A to form a $C_{3-12}$ cycloalkyl, 3-12 membered heteroalicyclic, $C_{6-12}$ aryl or 5-12 membered heteroaryl ring fused to A; and each hydrogen in $R^9$ and $R^{10}$ is optionally substituted by $R^3$;

each $R^{11}$ is independently halogen, $C_{1-12}$ alkyl, $C_{1-12}$ alkoxy, $C_{3-12}$ cycloalkyl, $C_{6-12}$ aryl, 3-12 membered heteroalicyclic, 5-12 membered heteroaryl, —O—$C_{1-12}$ alkyl, —O—$(CH_2)_nC_{3-12}$ cycloalkyl, —O—$(CH_2)_nC_{6-12}$ aryl, —O—$(CH_2)_n$(3-12 membered heteroalicyclic), —O—$(C_{1-12})_n$ (5-12 membered heteroaryl) or —CN, and each hydrogen in $R^{11}$ is optionally substituted by halogen, —OH, —CN, —$C_{1-12}$ alkyl which may be partially or fully halogenated, —O—$C_{1-12}$ alkyl which may be partially or fully halogenated, —CO, —SO or —$SO_2$;

each $R^{13}$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$S(O)_m$ $R^4$, —$SO_2NR^4R^5$, —$S(O)_2OR^4$, —$NO_2$, —$NR^4R^5$, —$(CR^6R^7)_nOR^4$, —CN, —$C(O)R^4$, —$OC(O)R^4$, —$O(CR^6R^7)_nR^4$, —$NR^4C(O)R^5$, —$(CR^6R^7)_nC(O)OR^4$, —$(CR^6R^7)_nOR^4$, —$(CR^6R^7)_nC(O)NR^4R^5$, —$(CR^6R^7)_n$ $NCR^4R^5$, —$C(=NR^6)NR^4R^5$, —$NR^4C(O)NR^5R^6$, —$NR^4S$ $(O)_pR^5$, —$C(O)NR^4R^5$, —$(CR^6R^7)_n$(3-12 membered heteroalicyclic), —$(CR^6R^7)_n(C_{3-12}$ cycloalkyl), —$(CR^6R^7)_n$ $(C_{6-12}$ aryl), —$(CR^6R^7)_n$(5-12 membered heteroaryl), —$(CR^6R^7)_nC(O)NR^4R^5$, or —$(CR^6R^7)_nC(O)R^4$, $R^{13}$ groups on adjacent atoms may combine to form a $C_{6-12}$ aryl, 5-12 membered heteroaryl, $C_{3-12}$ cycloalkyl or 3-12 membered heteroalicyclic group, and each hydrogen in $R^{13}$ is optionally substituted by $R^3$;

each m is independently 0, 1 or 2;
each n is independently 0, 1, 2, 3 or 4;
each p is independently 1 or 2;
or a pharmaceutically acceptable salt, hydrate or solvate thereof.

More particularly, preferred aminoheteroaryl compounds in the invention are selected from aminopyridine or aminopyrazine compounds.

The said aminoheteroaryl compound is preferably, according to an embodiment of the invention, selected from the group consisting of 5-Brom-3-[(R)-1-(2,6-dichloro-3-fluoro-phenyl)-ethoxy]-pyrazin-2-ylamine; 5-iodo-3-[(R)1-(2,6-dichloro-3-fluoro-phenyl)-ethoxy]-pyridin-2-ylamine; 5-bromo-3-[1(R)-(2,6-dichloro-3-fluoro-phenyl)-ethoxy]-pyridin-2-ylamine; 4-{5-Amino-6-[(R)-1-(2,6-dichloro-3-fluoro-phenyl)-ethoxy]-pyrazin-2-yl}-benzoic acid; (4-{5-Amino-6-[(R)-1-(2,6-dichloro-3-fluoro-phenyl)-ethoxy]-pyrazin-2-yl}-phenyl)-piperazin-1-yl-methanone; 4-(4-{5-Amino-6-[(R)-1-(2,6-dichloro-3-fluoro-phenyl)-ethoxy]-pyrazin-2-yl}-benzoyl)-piperazine-1-carboxylic acid terbutyl ester; 3-[(1R)-1-(2,6-dichloro-3-fluorophenyl)ethoxy]-5-[4-(piperazin-i-ylcarbonyl)phenyl]pyridin-2-anine; 4-{6-amino-5-[(1R)-1-(2,6-dichloro-3-fluorophenyl)ethoxy] pyridin-3-yl}-N-[2-(dimethylamino)ethyl]-N-methylbenzamide; (4-{6-amino-5-[(1R)-1-(2,6-dichloro-3-fluorophenyl)ethoxy]pyridin-3-yl}phenyl)methanol; (4-{6-amino-5-[(1R)-1-(2,6-dichloro-3-fluorophenyl)ethoxy] pyridin-3-yl}-N-[3-(dimethylamino)propyl]-N-methylbenzamide; tert-butyl 4-(4-{6-amino-5-[(1R)-1-(2,6-dichloro-3-fluorophenyl)ethoxy]pyridin-3-yl}benzoyl) piperazine-1-carboxylate; 3-[(R)-1-(2,6-Dichloro-3-fluoro-phenyl)-ethoxy]-5-[1-(1-methyl-piperidin-4-yl)-1H-pyrazol-4-yl]-pyridin-2-ylamine; 1-[4-(4-{6-Amino-5-[(R)-1-(2,6-dichloro-3-fluoro-phenyl)-ethoxy]-pyridin-3-yl}-pyrazol-1-yl)-piperidin-1-yl]-2-hydroxy-ethanone; 3-[(R)-1-(2,6-Dichloro-3-fluoro-phenyl)-ethoxy]-5-(1-piperidin-4-yl-1H-pyrazol-4-yl)-pyridin-2-ylamine; 3-[(R)-1-(2,6-Dichloro-3-fluoro-phenyl)-ethoxy]-5-(1-piperidin-4-yl-1H-pyrazol-4-yl)-pyrazin-2-ylamine; 3-[(R)-1-(2,6-Dichloro-3-fluoro-phenyl)-ethoxy]-5-(1H-pyrazol-4-yl)-pyrazin-2-ylamine: 1-[4-(4-{5-Amino-6-[(R)-1-(2,6-dichloro-3-fluoro-phenyl)-ethoxy]-pyrazin-2-yl}-pyrazol-1-yl)-piperidin-1-yl]-2-hydroxy-ethanone; 3-[(R)-1-(2,6-Dichloro-3-fluoro-phenyl)-ethoxy]-5-[1-(1-methyl-piperidin-4-yl)-1H-pyrazol-4-yl]-pyrazin-2-ylamine; 1-[4-(4-{5-Amino-6-[(R)-1-2,6-dichloro-3-fluoro-phenyl)-ethoxy]-pyrazin-2-yl}-pyrazol-1-yl)-piperidin-1-yl]-2-dimethylamino-ethanone; 3-[(R)-1-(2-Chloro-3,6-difluoro-phenyl)-ethoxy]-5-(1-piperidin-4-yl-1H-pyrazol-4-yl)pyridin-2-ylamine; or a pharmaceutically acceptable salt, solvate or hydrate thereof.

In another preferred embodiment of the invention, the aminoheteroaryl compound is a 3-[(R)-1-(2,6-Dichloro-3-fluoro-phenyl)-ethoxy]-5-(1-piperidin-4-yl-1H-pyrazol-4-yl)-pyridin-2-ylamine. Another name given to this chemical compound is PF-02341066 (also written PF-2341066).

This particular compound is described in details in Example 13 of the published patent application WO 2006/021884 and the process for its preparation is described in procedure 62 which is cited below.

General Procedure 62:

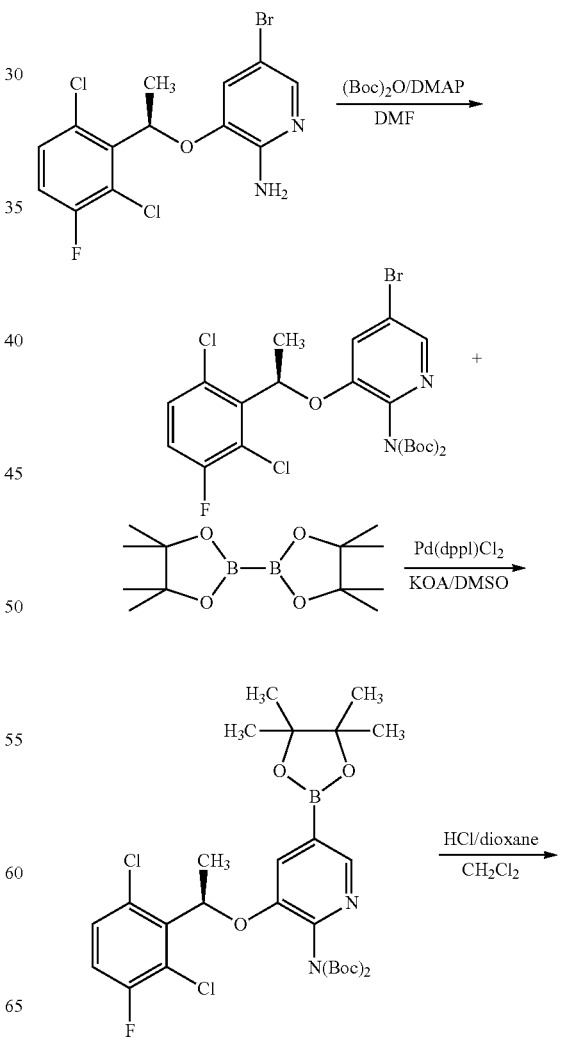

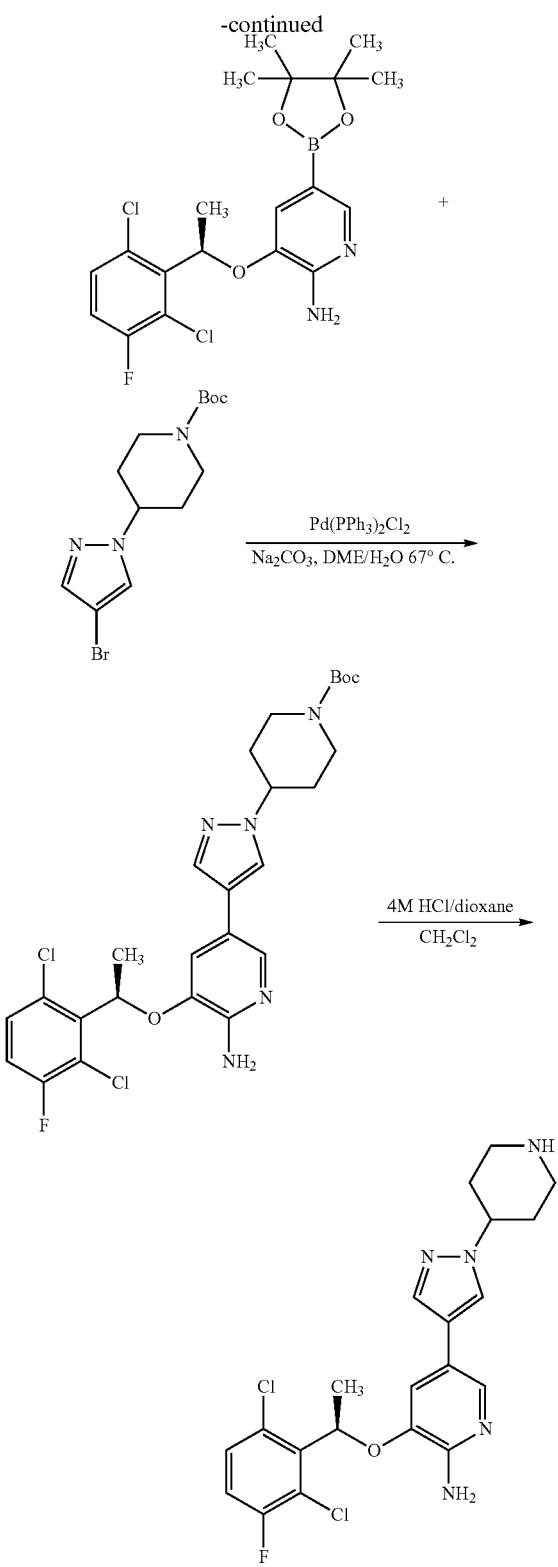

To a solution of 5-bromo-3-[(R)-1-(2,6-dichloro-3-fluoro-phenyl)-ethoxy]-pyridin-2-ylamine (12.83 g, 33.76 mmol) in anhydrous DMF (100 mL) was added di-tert-butyl dicarbonate (21.25 g, 97.35 mmol) and 4-dimethylami[pi]opyridine (0.793 g, 6.49 mmol). The reaction was stirred at ambient temperature for 18 hours under nitrogen. To the mixture was added saturated NaHCd$_3$ solution (300 mL), and extracted with EtOAc (3×250 mL). The combined extracts were washed with water (5×100 mL), sat. NaHCO$_3$, and brine, then dried over Na2SO4. After filtration, evaporation, and high vacuum drying, di-boc protected 5-bromo-3-[(R)-1-(2,6-dichloro-3-fluoro-phenyl)-ethoxy]-pyridin-2-ylamine was obtained as an off-white foam solid (19.59 g, 100% yield). $^1$H NMR (DMSO-d$_6$, 400 MHz) δ 8.18 (d, 1H), 7.83 (d, 1H), 7.59 (dd, 1H), 7.48 (t, 1H), 6.25 (q, 1H), 1.75 (d, 3H), 1.39 (s, 9H), 1.19 (s, 9H).

To a solution of the di-boc protected 5-bromo-3-[(R)-1-(2, 6-dichloro-3-fluoro-phenyl)-ethoxy]-pyridin-2-ylamine (19.58 g, 33.76 mmol) in DMSO (68 mL) was added potassium acetate (11.26 g, 114.78 mmol) and bis(pinacolato) diboron (10.29 g, 40.51 mmol). The mixture was degassed and charged with nitrogen three times, then Pd(dppf) Cl$_2$.CH$_2$Cl$_2$ (1.38 g, 1.69 mmol) was added. The reaction mixture was degassed and charged with nitrogen three times, and then stirred at 80° C. oil bath under nitrogen for 12 hours. The reaction was cooled to ambient temperature, diluted with ethyl acetate (100 mL), and filtered through a celite pad which was washed with ethyl acetate. The combined ethyl acetate solution (700 mL) was washed with water (5×100 mL), brine (100 mL), and dried over Na$_2$SO$_4$. After filtration and concentration, the residue was purified on a silica gel column eluting with EtOAc/Hexane (0%-50%) to provide di-boc protected 3-[(R)-1-(2,6-dichloro-3-fluoro-phenyl)-ethoxy]-5-(4,4,5,5-tetramethyl-[1,3,2]dioxaborolan-2-yl)-pyridin-2-ylamine as a foam sold (20.59 g, 97% yield). $^1$H NMR (DMSO-d$_6$, 400 MHz) δ 8.20 (d, 1H), 7.70 (d, 1H), 7.63 (dd, 1H) 1 7.47 (t, 1H), 6.20 (q, 1H), 1.73 (d, 3H), 1.50-1.13 (m, 30H).

To a solution of di-boc protected 3-[(R)-1-(2,6-dichloro-3-fluoro-phenyl)-ethoxy]-5-(4,4,5,5-tetramethyl-[1,3,2]dioxaborolan-2-yl)-pyridin-2-ylamine (20.34 g, 32.42 mmol) in CH$_2$Cl$_2$ (80 mL) was added a solution of dry HCl in dioxane (4N, 40.5 mL, 162 mmol). The reaction solution was stirred at 40° C. oil bath under nitrogen for 12 hours. The reaction mixture was cooled to ambient temperature, diluted with EtOAc (400 mL), then washed carefully but quickly with saturated NaHCO$_3$ until the water layer was basic (pH>8). The organic layer was washed with brine, and dried over Na$_2$SO$_4$. After filtration, evaporation, and high vacuum drying, 3-[(R)-1-(2,6-dichloro-3-fluoro-phenyl)-ethoxy]-5-(4,4, 5,5-tetramethyl-[1,3,2] dioxaborolan-2-yl)-pyridin-2-ylamine was obtained as an off-white foam solid (13.48 g, 97% yield). $^1$H NMR (DMSO-d$_6$, 400 MHz) δ 8.01 (d, 1H), 7.27 (dd, 1H), 7.17 (d, 1H), 7.03 (t, 1H), 6.12 (q, 1H), 5.08 (bs, 2H), 1.81 (d, 3H), 1.30 (s, 6H), 1.28 (s, 6H).

To a stirred solution of 3-[(R)-1-(2,6-dichloro-3-fluoro-phenyl)-ethoxy]-5-(4,4,5,5-tetramethyl-[1,3,2]dioxaborolan-2-yl)-pyridin-2-ylamine (4.2711 g, 10.0 mmol) and 4-(4-bromo-pyrazol-1-yl)-piperidine-1-carboxylic acid tert-butyl ester (3.9628 g, 12.0 mmol) in DME (40 mL) was added a solution of Na$_2$CO$_3$ (3.1787 g, 30.0 mmol) in water (10 mL). The solution was degassed and charged with nitrogen three times. To the solution was added Pd(PPh$_3$J$_2$Cl$_2$ (351 mg, 0.50 mmol). The reaction solution was degassed and charged with nitrogen again three times. The reaction solution was stirred at 87° C. oil bath for about 16 hours (or until consumption of the borane pinacol ester), cooled to ambient temperature and diluted with EtOAc (200 mL). The reaction mixture was filtered through a pad of celite and washed with EtOAc. The EtOAc solution was washed with brine, dried over Na$_2$SO$_4$, and concentrated. The crude product was purified on a silica gel column eluting with EtOAc/hexane system (0% EtOAc to 100% EtOAc) to afford 4-(4-{6-amino-5-[(R)-1-(2,6-dichloro-3-fluoro-phenyl)-ethoxy]-pyridin-3-yl}-pyrazol-1- yl)-piperidine-1-carboxylic acid tert-butyl ester (3.4167 g, 65% yield, ~95% purity) with a Rf of 0.15 (50% EtOAc/Hexanes). MS m/e 550 (M+1)⁺.

To a solution of 4-(4-{6-amino-5-[(R)-1-(2,6-dichloro-3-fluoro-phenyl)-ethoxy]-pyridin-3-yl}-pyrazol-1-yl)-piperidine-1-carboxylic acid tert-butyl ester (566.7 mg, 1.03 mmol) in methanol (5 mL) or dichlorometha[pi]e (30 mL) was added 4N HCl/dioxane (15 mL). The solution was stirred for about 1 hour or until the de-protection was complete. The solvents were evaporated and the residue was dissolved in methanol and purified on a reversed phase C-18 preparative HPLC eluting with acetonitrile/water with 0.1% acetic acid from 5% to 30% with a linear gradient. After lyophilization, 3-[(R)-1-(2,6-dichloro-3-fluoro-phenyl)-ethoxy]-5-(1-piperidin-4-yl-1H-pyrazol-4-yl)-pyridin-2-ylamine acetate was obtained as a white solid (410 mg, 78% yield, 100% HPLC purity, 96.4% ee). ¹H NMR (DMSO-d₆, 400 MHz) δ 7.84 (s, 1H), 7.68 (d, 1H), 7.50 (dd, 1H), 7.46 (s, 1H), 7.37 (t, 1H), 6.83 (d, 1H), 6.02 (q, 1H), 5.57 (bs, 2H), 4.09 (m, 1H), 2.98 (m, 2H), 2.53 (m, 2H), 1.88 (m, 2H), 1.82 (s, 3H), 1.73 (d, 3H), 1.70 (m, 2H). MS m/e 450 (M+1)⁺.

In a particular aspect of the invention, it is envisaged a composition of the present invention wherein said aminoheteroaryl compound is the compound of formula Ib:

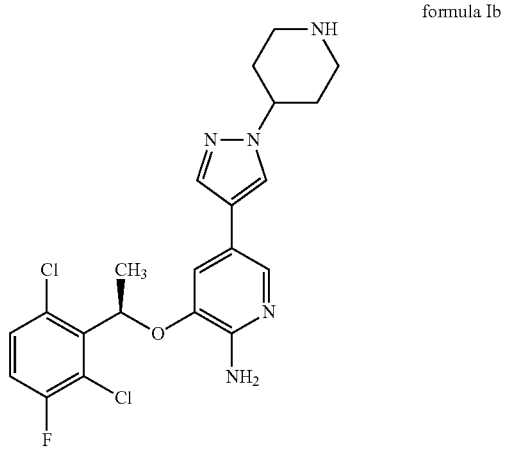 [SMILES: C[C@@H](Oc1cc(-c2cnn(C3CCNCC3)c2)cnc1N)c1c(Cl)ccc(F)c1Cl]

formula Ib

In another aspect, the invention concerns a method wherein said cancer is selected from cancers overexpressing c-Met and/or displaying an auto-phosphorylated c-Met.

More particularly, said cancer is selected from prostate cancer, osteosarcomas, lung cancer, breast cancer, endometrial cancer, glyoblastoma or colon cancer.

In a preferred embodiment, the invention relates to a composition as above mentioned, wherein said antibody antagonist to c-Met is selected from the 224G11, 227H1, 223C4 and 11E1 derived antibodies, or from the functional fragments thereof.

More particularly, the said antibody antagonist to c-Met is derived from the 224G11 antibody.

Still in another embodiment of the invention, it is described herein a composition, wherein said aminoheteroaryl compound is selected from aminopyridine or aminopyrazine compounds.

More particularly, the said aminoheteroaryl compound is the compound of formula Ib:

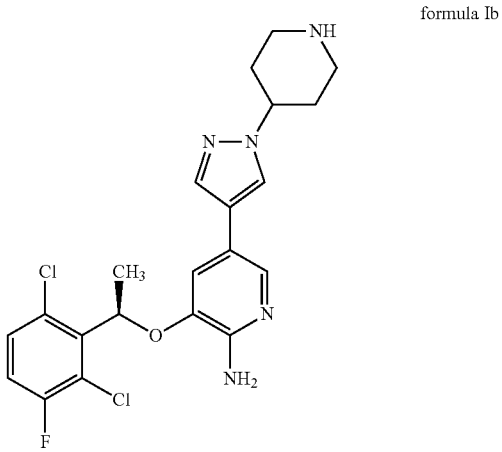 [SMILES: C[C@@H](Oc1cc(-c2cnn(C3CCNCC3)c2)cnc1N)c1c(Cl)ccc(F)c1Cl]

formula Ib

The invention also relates to the use of a composition as defined in the present application for treating cancer in a mammal.

In a particular preferred embodiment, said cancer is selected from cancers overexpressing c-Met and/or displaying an auto-phosphorylated c-Met. More particularly, said cancer is selected from prostate cancer, osteosarcomas, lung cancer, breast cancer, endometrial cancer, glyoblastoma or colon cancer.

Figure 2:
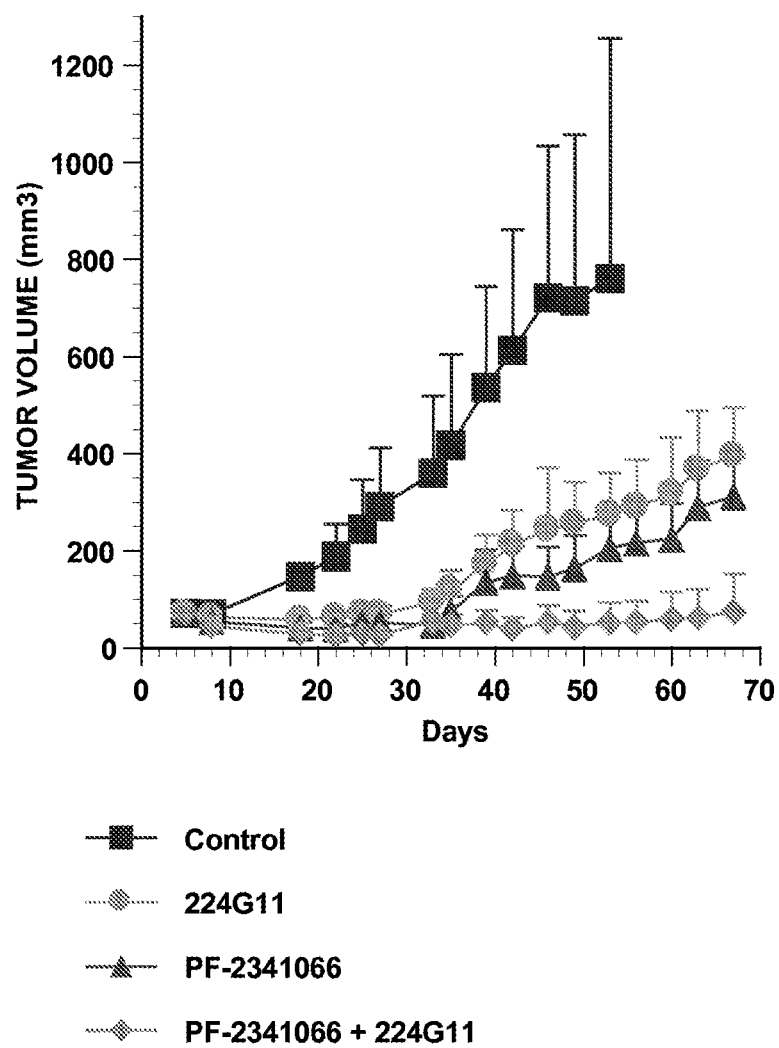

The invention will be better understood at the reading of the following examples wherein:

FIG. 1 illustrates the in vivo activity of 224G11 and the in vivo activity of PF-2341066 on NCI-H441 NSCLC, and FIG. 2 illustrates the synergic in vivo activity of a combination of 224G11 and PF-2341066 on NCI-H441 NSCLC.

EXAMPLE 1

In Vivo Activity of 224G11 and PF-02341066 as Single Treatments

In order to verify that the NCI-H441 in vivo model available in the laboratory is sensible to both the 224G11 antibody and the PF-2341066 compound, immunocompromised mice engrafted subcutaneously with NCI-H441 were used. Briefly, NCI-H441 NSCLC cells from ATCC were cultured in RPMI 1640 medium, 10% FCS, 1% L-Glutamine. Cells were split two days before engraftment so that they were in exponential phase of growth. Ten million NCI-H441 cells were injected s.c. to Athymic nude mice. Five days after implantation, tumors were measurable and animals were divided into groups of 6 mice with comparable tumor size. For the antibody treatment, mice were treated i.p. with a loading dose of 2 mg of 224G11 Mab/mouse and then twice a week with 1 mg of antibody/mouse. 50 mg/kg of PF-02341066 was administered p.o. (oral gavage), daily for a week and then 5 days a week with a double dose the fifth day. Treatment lasted during the whole experiment. Tumor volume was measured twice a week and calculated by the formula: π/6×length×width×height.

Results described in FIG. 1 showed a significant difference in tumors growth of mice treated both with 224G11 and PF-02341066. In this experiment 224G11 and PF2341066 showed comparable antitumoral activities.

EXAMPLE 2

In Vivo Activity of a Combination of 224G11 and PF-02341066

NCI-H441 cells from ATCC were routinely cultured in RPMI 1640 medium, 10% FCS, 1% L-Glutamine. Cells were split two days before engraftment so that they were in exponential phase of growth. Ten million NCI-H441 cells were engrafted to Athymic nude mice. Five days after implantation, tumors were measurable and animals were divided into groups of 6 mice with comparable tumor size. For the antibody treatment, mice were treated i.p. with a loading dose of 2 mg of 224G11 Mab/mouse and then twice a week with 1 mg of antibody/mouse. 50 mg/kg of PF-2341066 was administered p.o. (oral gavage), daily for a week and then 5 days a week with a double dose the fifth day. The group of mice receiving both 224G11 and PF-2341066 was treated following the same modalities as the one described above for each compound. Tumor volume was measured twice a week and calculated by the formula: $\pi/6 \times length \times width \times height$ and animal weights were monitored every day over the period of treatment.

Statistical analysis was performed at each measured time using a Mann-Whitney test. In this experiment, mice of the control group were sacrificed on day 53 for ethical reasons. At day 53 post first injection, the average tumor volume of single modality treated groups is reduced by 64%, 73% and 93% for 224G11, PF-2341066 and 224G11+PF-2341066 respectively. At Day 53, the combined therapy improved significantly tumor growth compared to single therapy treatments ($p \leq 0.002$ compared to PF-2341066 alone and $p \leq 0.002$ compared to 224G11 alone), 1 out of 6 mice being without tumor in the combined therapy group. No significant differences were observed between the 2 single modality treatment.

These results, represented at FIG. 2, were confirmed 14 days after the end of treatments (D67) where tumor volume of the group receiving the combination therapy remained significantly lower than the ones injected with the single modality treatment and where 16% of mice receiving the combined treatment were still tumor free.

---

The invention claimed is:

1. A composition comprising an antibody antagonist to c-Met, or a cMet-binding fragment thereof, and an aminoheteroaryl compound, wherein:

i) said antibody antagonist to c-Met comprises a heavy chain comprising CDR-H1, CDR-H2 and CDR-H3 comprising, respectively, the amino acid sequences SEQ ID Nos. 1, 2 and 3; and a light chain comprising CDR-L1, CDR-L2 and CDR-L3 comprising, respectively, the amino acid sequences SEQ ID Nos. 10, 11 and 12; and ii) said aminoheteroaryl compound is selected from the group consisting of compounds of formula I:

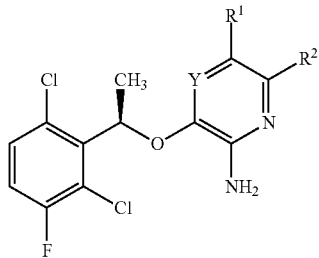

Formula I wherein:

Y is N or $CR^{12}$;

$R^1$ is hydrogen, halogen, $C_{6-12}$ aryl, 5-12 membered heteroaryl, $C_{3-12}$ cycloalkyl, 3-12 membered heteroalicyclic, $-O(CR^6R^7)_nR^4$, $-C(O)R^4$, $-C(O)OR^4$, $-CN$, $-NO^2$, $-S(O)_mR^4$, $-SO_2NR^4R^5$, $-C(O)NR^4R^5$, $-NR^4C(O)R^5$, $-C(=NR^6)NR^4R^5$, $C_{1-8}$ alkyl, $C_{2-8}$ alkenyl, or $C_{2-8}$ alkynyl; and each hydrogen in $R^1$ is optionally substituted by one or more $R^3$ groups;

$R^2$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, $-S(O)_m R^4$, $-SO_2NR^4R^5$, $-S(O)_2OR^4$, $-NO_2$, $-NR^4R^5$, $-(CR^6R^7)_nOR^4$, $-CN$, $-C(O)R^4$, $-OC(O)R^4$, $-O(CR^6R^7)_nR^4$, $-NR^4C(O)R^5$, $-(CR^6R^7)_nC(O)OR^4$, $-(CR^6R^7)_nNC^R4R^5$, $-C(=NR^6)NR^4R^5$, $-NR^4C(O)NR^5R^6$, $-NR^4S(O)_pR^5$ or $-C(O)NR^4R^5$, and each hydrogen in $R^2$ is optionally substituted by $R^8$;

each $R^3$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, $-S(O)_m R^4$, $-SO_2NR^4R^5$, $-S(O)2OR^4$, $-NO_2$, $-NR^4R^5$, $-(CR^6R^7)_nOR^4$, $-CN$, $-C(O)R^4$, $-OC(O)R^4$, $-O(CR^6R^7)_nR^4$, $-NR^4C(O)R^5$, $-(CR^6R^7)_nC(O)OR^4$, $-(CR^6R^7)_nOR^4$, $-(CR^6R^7)_nC(O)NR^4R^5$, $-(CR^6R^7)_nNCR^4R^5$, $-C(=NR^6)NR^4R^5$, $-NR^4C(O)NR^5R^6$, $-NR^4S(O)_pR^5$ or $-C(O)NR^4R^5$, each hydrogen in $R^3$ is optionally substituted by $R^8$, and $R^3$ groups on adjacent atoms may combine to form a $C_{6-12}$ aryl, 5-12 membered heteroaryl, $C_{3-12}$ cycloalkyl or 3-12 membered heteroalicyclic group;

each $R^4$, $R^5$, $R^6$ and $R^7$ is independently hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl; or any two of $R^4$, $R^5$, $R^6$ and $R^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of $R^4$, $R^5$, $R^6$ and $R^7$ bound to the same carbon atom may be combined to form a $C_{3-12}$ cycloalkyl, $C_{6-12}$ aryl, 3-12 membered heteroalicyclic or 5-12 membered heteroaryl group; and each hydrogen in $R^4$, $R^5$, $R^6$ and $R^7$ is optionally substituted by $R^8$;

each $R^8$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$NH_2$, —CN, —OH, —O—$C_{1-12}$ alkyl, —O—$(CH_2)_nC_{3-12}$ cycloalkyl, —O—$(CH_2)_nC_{6-12}$ aryl, —O—$(CH_2)_n$(3-12 membered heteroalicyclic) or —O—(CH2)n(5-12 membered heteroaryl); and each hydrogen in $R^8$ is optionally substituted by $R^{11}$;

each $R^9$ and $R^{10}$ is independently hydrogen, halogen, $C_{1-12}$ alkyl, $C_{3-12}$ cycloalkyl, $C_{6-12}$ aryl, 3-12 membered heteroalicyclic, 5-12 membered heteroaryl, —$S(O)_mR^4$, —$SO_2NR^4R^5$, —$S(O)_2OR^4$, —$NO_2$, —$NR^4R^5$, —$(CR^6R^7)_nOR^4$, —CN, —$C(O)R^4$, —OC(O)$R^4$, —$NR^4C(O)R^5$, —$(CR^6R^7)_nC(O)OR^4$, —$(CR^6R^7)_nNCR^4R^5$, —$NR^4C(O)NR^5R^6$, —$NR^4S(O)_pR^5$ or —$C(O)NR^4R^5$; $R^9$ or $R^{10}$ may combine with a ring atom of A or a substituent of A to form a $C_{3-12}$ cycloalkyl, 3-12 membered heteroalicyclic, $C_{6-12}$ aryl or 5-12 membered heteroaryl ring fused to A; and each hydrogen in $R^9$ and $R^{10}$ is optionally substituted by $R^3$;

each $R^{11}$ is independently halogen, $C_{1-12}$ alkyl, $C_{1-12}$ alkoxy, $C_{3-12}$ cycloalkyl, $C_{6-12}$ aryl, 3-12 membered heteroalicyclic, 5-12 membered heteroaryl, —O—$C_{1-12}$ alkyl, —O—$(CH_2)_nC_{3-12}$ cycloalkyl, —O—$(CH_2)$n$C_{6-12}$ aryl, —O—$(CH_2)_n$(3-12 membered heteroalicyclic), —O—$(CH_2)_n$(5-12 membered heteroaryl) or —CN, and each hydrogen in $R^{11}$ is optionally substituted by halogen, —OH, —CN, —$C_{1-12}$ alkyl which may be partially or fully halogenated, —O-$C_{1-12}$ alkyl which may be partially or fully halogenated, —CO, —SO or —$SO_2$;

$R^{12}$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$S(O)_mR^4$, —$SO_2NR^4R^5$, —$S(O)_2OR^4$, —$NO_2$, —$NR^4R^5$, —$(CR^6R^7)_nOR^4$, —CN, —$C(O)R^4$, —OC(O)$R^4$, —O(CR^6R^7)_nR^4$, —$NR^4C(O)R^5$, —$(CR^6R^7)_nC(O)OR^4$, —$(CR^6R^7)_nNCR^4R^5$, —$C(=NR^6)NR^4R^5$, —$NR^4C(O)NR^5R^6$, —$NR^4S(O)_pR^5$ or —$C(O)NR^4R^5$, and each hydrogen in $R^{12}$ is optionally substituted by $R^3$;

each $R^{13}$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$S(O)_mR^4$, —$SO_2NR^4R^5$, —$S(O)_2OR^4$, —$NO_2$,—$NR^4R^5$, —$(CR^6R^7)_nOR^4$, —CN, —$C(O)R^4$, —OC(O)$R^4$, —O$(CR^6R^7)_nR^4$, —$NR^4C(O)R^5$, —$(CR^6R^7)_nC(O)OR^4$,—$(CR^6R^7)_nOR^4$, —$(CR^6R^7)_nC(O)NR^4R^5$, —$(CR^6R^7)_nNCR^4R^5$, —$C(=NR^6)NR^4R^5$, —$NR^4C(O)NR^5R^6$, —$NR^4S(O)_pR^5$, —$C(O)NR^4R^5$, —$(CR^6R^7)_n$(3-12membered heteroalicyclic), —$(CR^6R^7)_n(C_{3-12}$ cycloalkyl), —$(CR^6R^7)_n(C_{6-12}$ aryl), —$(CR^6R^7)_n$(5-12 membered heteroaryl), —$(CR^6R^7)_nC(O)NR^4R^5$, or —$(CR^6R^7)_nC(O)R^4$, $R^{13}$ groups on adjacent atoms may combine to form a $C_{6-12}$ aryl, 5-12 membered heteroaryl, $C_{3-12}$ cycloalkyl or 3-12 membered heteroalicyclic group, and each hydrogen in $R^{13}$ is optionally substituted by $R^3$;

each m is independently 0, 1 or 2;
each n is independently 0, 1, 2, 3 or 4;
each p is independently 1 or 2;
and a pharmaceutically acceptable salt, hydrate or solvate thereof.

2. The composition according to claim 1, wherein the composition is a pharmaceutical composition.

3. A pharmaceutical composition comprising at least:
i) one antibody antagonist to c-Met, or a cMet-binding fragment thereof; and
ii) an aminoheteroaryl compound,
as combination products for simultaneous, separate or sequential use; wherein:
i) said antibody antagonist to c-Met comprises a heavy chain comprising CDR-H1, CDR-H2 and CDR-H3 comprising, respectively, the amino acid sequences SEQ ID Nos. 1, 2 and 3; and a light chain comprising CDR-L1, CDR-L2 and CDR-L3 comprising, respectively, the amino acid sequences SEQ ID Nos. 10, 11 and 12;
and
ii) said aminoheteroaryl compound is selected from the group consisting of compounds of formula I:

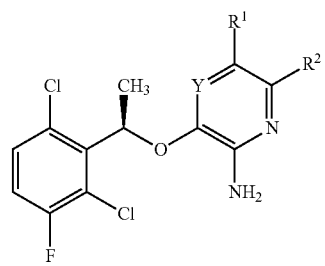

Formula I wherein:
Y is N or $CR^{12}$;
$R^1$ is hydrogen, halogen, $C_{6-12}$ aryl, 5-12 membered heteroaryl, $C_{3-12}$ cycloalkyl, 3-12 membered heteroalicyclic, —$O(CR^6R^7)_nR^4$, —$C(O)R^4$, —$C(O)OR^4$, —CN, —$NO^2$, —$S(O)_mR^4$, —$SO_2NR^4R^5$, —$C(O)NR^4R^5$, —$NR^4C(O)R^5$, —$C(=NR^6)NR^4R^5$, $C_{1-8}$ alkyl, $C_{2-8}$ alkenyl, or $C_{2-8}$ alkynyl; and each hydrogen in $R^1$ is optionally substituted by one or more $R^3$ groups;

$R^2$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$S(O)_m$ $R^4$, —$SO_2NR^4R^5$, —$S(O)_2OR^4$, —$NO_2$, —$NR^4R^5$, —$(CR^6R^7)_nOR^4$, —CN, —$C(O)R^4$, —OC(O)$R^4$, —O$(CR^6R^7)_nR^4$, —$NR^4C(O)R^5$, —$(CR^6R^7)_nC(O)OR^4$, —$(CR^6R^7)_nNC^R4R^5$, —$C(=NR^6)NR^4R^5$, —$NR^4C(O)NR^5R^6$, —$NR^4S(O)_pR^5$ or —$C(O)NR^4R^5$, and each hydrogen in $R^2$ is optionally substituted by $R^8$;

each $R^3$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$S(O)_mR^4$, —$SO_2NR^4R^5$,—$S(O)2OR^4$, —$NO_2$, —$NR^4R^5$, —$(CR^6R^7)_nOR^4$, —CN, —$C(O)$ R⁴, —OC(O)R⁴, —O(CR⁶R⁷)ₙR⁴, —NR⁴C(O)R⁵, —(CR⁶R⁷)ₙC(O)OR⁴, —(CR⁶R⁷)ₙOR⁴, —(CR⁶R⁷)ₙC(O)NR⁴R⁵, —(CR⁶R⁷)ₙNCR⁴R⁵, —C(=NR⁶)NR⁴R⁵, —NR⁴C(O)NR⁵R⁶, —NR⁴S(O)ₚR⁵ or —C(O)NR⁴R⁵, each hydrogen in R³ is optionally substituted by R⁸, and R³ groups on adjacent atoms may combine to form a C₆₋₁₂ aryl, 5-12 membered heteroaryl, C₃₋₁₂ cycloalkyl or 3-12 membered heteroalicyclic group;

each R⁴, R⁵, R⁶ and R⁷ is independently hydrogen, halogen, C₁₋₁₂ alkyl, C₂₋₁₂ alkenyl, C₂₋₁₂ alkynyl, C₃₋₁₂ cycloalkyl, C₆₋₁₂ aryl, 3-12 membered heteroalicyclic, 5-12 membered heteroaryl; or any two of R⁴, R⁵, R⁶ and R⁷ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of R⁴, R⁵, R⁶ and R⁷ bound to the same carbon atom may be combined to form a C₃₋₁₂ cycloalkyl, C₆₋₁₂ aryl, 3-12 membered heteroalicyclic or 5-12 membered heteroaryl group; and each hydrogen in R⁴, R⁵, R⁶ and R⁷ is optionally substituted by R⁸;

each R⁸ is independently halogen, C₁₋₁₂ alkyl, C₂₋₁₂ alkenyl, C₂₋₁₂ alkynyl, C₃₋₁₂ cycloalkyl, C₆₋₁₂ aryl, 3-12 membered heteroalicyclic, 5-12 membered heteroaryl, —NH₂, —CN, —OH, —O—C₁₋₁₂ alkyl, —O—(CH₂)ₙC₃₋₁₂ cycloalkyl, —O—(CH₂)ₙC₆₋₁₂ aryl, —O—(CH₂)ₙ(3-12 membered heteroalicyclic) or —O—(CH2)n(5-12 membered heteroaryl); and each hydrogen in R⁸ is optionally substituted by R¹¹;

each R⁹ and R¹⁰ is independently hydrogen, halogen, C₁₋₁₂ alkyl, C₃₋₁₂ cycloalkyl, C₆₋₁₂ aryl, 3-12 membered heteroalicyclic, 5-12 membered heteroaryl, —S(O)ₘR⁴, —SO₂NR⁴R⁵, —S(O)₂OR⁴, —NO2, —NR⁴R⁵, —(CR⁶R⁷)ₙOR⁴, —CN, —C(O)R⁴, —OC(O)R⁴, —NR⁴C(O)R⁵, —(CR⁶R⁷)ₙC(O)OR⁴, —(CR⁶R⁷)ₙNCR⁴R⁵, —NR⁴C(O)NR⁵R⁶, —NR⁴S(O)ₚR⁵ or —C(O)NR⁴R⁵; R⁹ or R¹⁰ may combine with a ring atom of A or a substituent of A to form a C₃₋₁₂ cycloalkyl, 3-12 membered heteroalicyclic, C₆₋₁₂ aryl or 5-12 membered heteroaryl ring fused to A; and each hydrogen in R⁹ and R¹⁰ is optionally substituted by R³;

each R¹¹ is independently halogen, C₁₋₁₂ alkyl, C₁₋₁₂ alkoxy, C₃₋₁₂ cycloalkyl, C₆₋₁₂ aryl, 3-12 membered heteroalicyclic, 5-12 membered heteroaryl, —O—C₁₋₁₂ alkyl, —O—(CH₂)ₙC₃₋₁₂ cycloalkyl, —O—(CH₂)nC₆₋₁₂ aryl, —O—(CH₂)ₙ(3-12 membered heteroalicyclic), —O—(CH₂)ₙ(5-12 membered heteroaryl) or —CN, and each hydrogen in R¹¹ is optionally substituted by halogen, —OH, —CN, —C₁₋₁₂ alkyl which may be partially or fully halogenated, —O—C₁₋₁₂ alkyl which may be partially or fully halogenated, —CO, —SO or —SO₂;

R¹² is hydrogen, halogen, C₁₋₁₂ alkyl, C₂₋₁₂ alkenyl, C₂₋₁₂ alkynyl, C₃₋₁₂ cycloalkyl, C₆₋₁₂ aryl, 3-12 membered heteroalicyclic, 5-12 membered heteroaryl, —S(O)ₘR⁴, —SO₂NR⁴R⁵, —S(O)₂OR⁴, —NO₂, —NR⁴R⁵, —(CR⁶R⁷)ₙOR⁴, —CN, —C(O)R⁴, —OC(O)R⁴, —O(CR⁶R⁷)ₙR⁴, —NR⁴C(O)R⁵, —(CR⁶R⁷)ₙC(O)OR⁴, —(CR⁶R⁷)ₙNCR⁴R⁵, —C(=NR⁶)NR⁴R⁵, —NR⁴C(O)NR⁵R⁶, —NR⁴S(O)ₚR⁵ or —C(O)NR⁴R⁵, and each hydrogen in R¹² is optionally substituted by R³;

each R¹³ is independently halogen, C₁₋₁₂ alkyl, C₂₋₁₂ alkenyl, C₂₋₁₂ alkynyl, C₃₋₁₂ cycloalkyl, C₆₋₁₂ aryl, 3-12 membered heteroalicyclic, 5-12 membered heteroaryl, —S(O)ₘR⁴, —SO₂NR⁴R⁵, —S(O)₂OR⁴, —NO₂, —NR⁴R⁵, —(CR⁶R⁷)ₙOR⁴, —CN, —C(O)R⁴, —OC(O)R⁴, —O(CR⁶R⁷)ₙR⁴, —NR⁴C(O)R⁵, —(CR⁶R⁷)ₙC(O)OR⁴, —(CR⁶R⁷)ₙOR⁴, —(CR⁶R⁷)ₙC(O)NR⁴R⁵, —(CR⁶R⁷)ₙNCR⁴R⁵, —C(=NR⁶)NR⁴R⁵, —NR⁴C(O)NR⁵R⁶, —NR⁴S(O)ₚR⁵, 13 C(O)NR⁴R⁵, —(CR⁶R⁷),(3-12 membered heteroalicyclic), —(CR⁶R⁷)ₙC₃₋₁₂ cycloalkyl), —(CR⁶R⁷)ₙC₆₋₁₂ aryl), —(CR⁶R⁷)ₙ(5-12 membered heteroaryl), —(CR⁶R⁷)ₙC(O)NR⁴R⁵, or —(CR⁶R⁷)ₙC(O)R⁴, R¹³ groups on adjacent atoms may combine to form a C₆₋₁₂ aryl, 5-12 membered heteroaryl, C₃₋₁₂ cycloalkyl or 3-12 membered heteroalicyclic group, and each hydrogen in R¹³ is optionally substituted by R³;

each m is independently 0, 1 or 2;
each n is independently 0, 1, 2, 3 or 4;
each p is independently 1 or 2;
and a pharmaceutically acceptable salt, hydrate or solvate thereof.

4. The composition according to one of claims 1 to 3, wherein said antibody antagonist to c-Met, or a cMet-binding fragment thereof, is an antibody, or a cMet-binding fragment thereof, comprising a heavy chain comprising the amino acid sequence SEQ ID No. 18 and a light chain comprising the amino acid sequence SEQ ID No. 21.

5. The composition according to anyone of claims 1-3, wherein said antibody antagonist to c-Met, or a cMet-binding thereof, is the 224G11 monoclonal antibody, or a cMet-binding fragment thereof, secreted by the hybridoma deposited at CNCM on Mar. 14, 2007 under the number I-3731.

6. The composition according to any one of claims 1 to 3, wherein said aminoheteroaryl compound is the compound of formula Ib, 3-[(R)-1-(2,6-Dichloro-3-fluoro-phenyl)-ethoxy]-5-(1-piperidin-4-yl-1H-pyrazol-4-yl)-pyridin-2-ylamine:

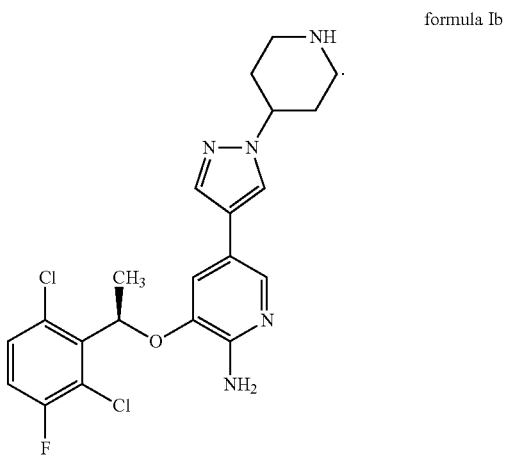 [SMILES: C[C@@H](Oc1cc(-c2cnn(C3CCNCC3)c2)cnc1N)c1c(Cl)ccc(F)c1Cl]

formula Ib

7. A method for treating cancer comprising the administration to a subject in need of treatment for cancer of a therapeutically effective amount of a composition according to any one of the claims 1 to 3.

8. A method for treating cancer comprising the administration to a subject in need of treatment for cancer of a therapeutically effective amount of a composition according to claim 3.

9. The method according to claim 7, wherein said cancer is chosen from cancers overexpressing c-Met and/or displaying an auto-phosphorylated c-Met.

10. The method according to claim 7, wherein said cancer is chosen from prostate cancer, osteosarcomas, lung cancer, breast cancer, endometrial cancer, glyoblastoma, and colon cancer.

11. The method according to claim 7 wherein the subject is a mammal.

12. The method according to claim 8, wherein said cancer is chosen from cancers overexpressing c-Met and/or displaying an auto-phosphorylated c-Met.

13. The method according to claim 8, wherein said cancer is chosen from prostate cancer, osteosarcomas, lung cancer, breast cancer, endometrial cancer, glyoblastoma, and colon cancer.

14. The method according to claim 11, wherein the mammal is a human.

15. The method according to claim 8, wherein the subject is a mammal.

16. The method according to claim 15, wherein the mammal is a human.

17. A method for treating cancer comprising the administration to a human in need of treatment of cancer of a therapeutically effective amount of:
   i) an antibody antagonist to c-Met, or a cMet-binding fragment thereof; and
   ii) an aminoheteroaryl compound, wherein
   i) said antibody antagonist to c-Met comprises a heavy chain comprising CDR-H1, CDR-H2 and CDR-H3 comprising, respectively, the amino acid sequences SEQ ID Nos. 1, 2 and 3; and a light chain comprising CDR-L1, CDR-L2 and CDR-L3 comprising, respectively, the amino acid sequences SEQ ID Nos. 10, 11 and 12;
   ii) said aminoheteroaryl compound is the compound of formula Ib, 3-[(R)-1-(2,6-Dichloro-3-fluoro-phenyl)-ethoxy]-5-(1-piperidin in-4-yl-1H-pyrazol-4-yl)-pyridin-2-ylamine:

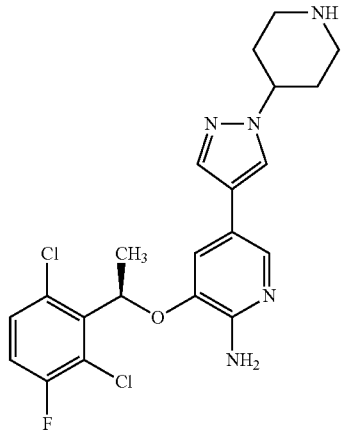 [SMILES: C[C@@H](Oc1cc(-c2cnn(C3CCNCC3)c2)cnc1N)c1c(Cl)ccc(F)c1Cl]

formula Ib; and
said cancer is lung cancer.

* * * * *

UNITED STATES PATENT AND TRADEMARK OFFICE
CERTIFICATE OF CORRECTION

| | | |
|---|---|---|
| PATENT NO. | : 8,623,359 B2 | Page 1 of 1 |
| APPLICATION NO. | : 13/002875 | |
| DATED | : January 7, 2014 | |
| INVENTOR(S) | : Liliane Goetsch | |

It is certified that error appears in the above-identified patent and that said Letters Patent is hereby corrected as shown below:

In the Claims

In claim 1, column 41, lines 65-66,
"-$(CR^6R^7)_n$(3-12membered heteroalicyclic)," should read
-- -$(CR^6R^7)_n$(3-12 membered heteroalicyclic),--.

In claim 3, column 43, line 7, "5-12membered" should read --5-12 membered--.

In claim 3, column 44, line 9, after "-$NR^4S(O)_pR^5$," delete "13".

In claim 3, column 44, line 10, "$C(O)NR^4R^5$" should read -- -$C(O)NR^4R^5$--.

In claim 3, column 44, lines 10-11,
"-$(CR^6R^7)$,(3-12 membered heteroalicyclic)," should read
-- -$(CR^6R^7)_n$(3-12 membered heteroalicyclic),--.

In claim 17, column 46, lines 6-8,
"3-[(R)-1-(2,6-Dichloro-3-fluoro-phenyl)-ethoxy]-5-(1-piperidin in-4-yl-1H-pyrazol-4-yl)-pyridin-2-ylamine:" should read
--3-[(R)-1-(2,6-Dichloro-3-fluoro-phenyl)-ethoxy]-5-(1-piperidin-4-yl-1H-pyrazol-4-yl)-pyridin-2-ylamine:--.

Signed and Sealed this
Twenty-fourth Day of June, 2014

Michelle K. Lee
*Deputy Director of the United States Patent and Trademark Office*

SEQUENCE LISTING

```
<160> NUMBER OF SEQ ID NOS: 62

<210> SEQ ID NO 1
<211> LENGTH: 8
<212> TYPE: PRT
<213> ORGANISM: mus musculus

<400> SEQUENCE: 1

Gly Tyr Ile Phe Thr Ala Tyr Thr
1               5

<210> SEQ ID NO 2
<211> LENGTH: 8
<212> TYPE: PRT
<213> ORGANISM: mis musculus

<400> SEQUENCE: 2

Ile Lys Pro Asn Asn Gly Leu Ala
1               5

<210> SEQ ID NO 3
<211> LENGTH: 11
<212> TYPE: PRT
<213> ORGANISM: mus musculus

<400> SEQUENCE: 3

Ala Arg Ser Glu Ile Thr Thr Glu Phe Asp Tyr
1               5                   10

<210> SEQ ID NO 4
<211> LENGTH: 8
<212> TYPE: PRT
<213> ORGANISM: mus musculus

<400> SEQUENCE: 4

Gly Tyr Ser Phe Thr Asp Tyr Thr
1               5

<210> SEQ ID NO 5
<211> LENGTH: 8
<212> TYPE: PRT
<213> ORGANISM: mus musculus
```

```
<400> SEQUENCE: 5

Ile Asn Pro Tyr Asn Gly Gly Thr
1               5

<210> SEQ ID NO 6
<211> LENGTH: 11
<212> TYPE: PRT
<213> ORGANISM: mus musculus

<400> SEQUENCE: 6

Ala Arg Glu Glu Ile Thr Lys Asp Phe Asp Phe
1               5                   10

<210> SEQ ID NO 7
<211> LENGTH: 8
<212> TYPE: PRT
<213> ORGANISM: mus musculus

<400> SEQUENCE: 7

Gly Tyr Thr Phe Thr Asp Tyr Asn
1               5

<210> SEQ ID NO 8
<211> LENGTH: 8
<212> TYPE: PRT
<213> ORGANISM: mus musculus

<400> SEQUENCE: 8

Ile Asn Pro Asn Asn Gly Gly Thr
1               5

<210> SEQ ID NO 9
<211> LENGTH: 14
<212> TYPE: PRT
<213> ORGANISM: mus musculus

<400> SEQUENCE: 9

Ala Arg Gly Arg Tyr Val Gly Tyr Tyr Ala Met Asp Tyr
1               5                   10

<210> SEQ ID NO 10
<211> LENGTH: 10
<212> TYPE: PRT
<213> ORGANISM: mus musculus

<400> SEQUENCE: 10

Glu Ser Val Asp Ser Tyr Ala Asn Ser Phe
1               5                   10

<210> SEQ ID NO 11
<211> LENGTH: 3
<212> TYPE: PRT
<213> ORGANISM: mus musculus

<400> SEQUENCE: 11

Arg Ala Ser
1

<210> SEQ ID NO 12
<211> LENGTH: 9
<212> TYPE: PRT
<213> ORGANISM: mus musculus

<400> SEQUENCE: 12
```

-continued

Gln Gln Ser Lys Glu Asp Pro Leu Thr
1               5

<210> SEQ ID NO 13
<211> LENGTH: 10
<212> TYPE: PRT
<213> ORGANISM: mus musculus

<400> SEQUENCE: 13

Glu Ser Ile Asp Thr Tyr Gly Asn Ser Phe
1               5                   10

<210> SEQ ID NO 14
<211> LENGTH: 9
<212> TYPE: PRT
<213> ORGANISM: mus musculus

<400> SEQUENCE: 14

Gln Gln Ser Asn Glu Asp Pro Phe Thr
1               5

<210> SEQ ID NO 15
<211> LENGTH: 6
<212> TYPE: PRT
<213> ORGANISM: mus musculus

<400> SEQUENCE: 15

Glu Asn Ile Tyr Ser Asn
1               5

<210> SEQ ID NO 16
<211> LENGTH: 3
<212> TYPE: PRT
<213> ORGANISM: mus musculus

<400> SEQUENCE: 16

Ala Ala Thr
1

<210> SEQ ID NO 17
<211> LENGTH: 9
<212> TYPE: PRT
<213> ORGANISM: mus musculus

<400> SEQUENCE: 17

Gln His Phe Trp Gly Pro Pro Tyr Thr
1               5

<210> SEQ ID NO 18
<211> LENGTH: 118
<212> TYPE: PRT
<213> ORGANISM: mus musculus

<400> SEQUENCE: 18

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
        35                  40                  45

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Ser Thr Ala Tyr
65                  70                  75                  80

-continued

```
Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser
        115

<210> SEQ ID NO 19
<211> LENGTH: 118
<212> TYPE: PRT
<213> ORGANISM: mus musculus

<400> SEQUENCE: 19

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Asp Tyr
            20                  25                  30

Thr Leu Asn Trp Val Lys Gln Ser His Gly Lys Thr Leu Glu Trp Ile
        35                  40                  45

Gly Leu Ile Asn Pro Tyr Asn Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Glu Glu Ile Thr Lys Asp Phe Asp Phe Trp Gly Gln Gly Thr
            100                 105                 110

Thr Leu Thr Val Ser Ser
        115

<210> SEQ ID NO 20
<211> LENGTH: 121
<212> TYPE: PRT
<213> ORGANISM: mus musculus

<400> SEQUENCE: 20

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Met Ser Leu Glu Trp Ile
        35                  40                  45

Gly Asp Ile Asn Pro Asn Asn Gly Gly Thr Ile Phe Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Gly Arg Tyr Val Gly Tyr Tyr Tyr Ala Met Asp Tyr Trp Gly
            100                 105                 110

Gln Gly Thr Ser Val Thr Val Ser Ser
        115                 120

<210> SEQ ID NO 21
<211> LENGTH: 111
<212> TYPE: PRT
<213> ORGANISM: mus musculus
```

-continued

<400> SEQUENCE: 21

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Ala Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Val Ala Thr Tyr Tyr Cys Gln Gln Ser Lys
                85                  90                  95

Glu Asp Pro Leu Thr Phe Gly Ser Gly Thr Lys Leu Glu Met Lys
            100                 105                 110

<210> SEQ ID NO 22
<211> LENGTH: 111
<212> TYPE: PRT
<213> ORGANISM: mus musculus

<400> SEQUENCE: 22

Gly Ile Val Leu Thr Gln Ser Pro Ala Ser Leu Ala Val Ser Leu Gly
1               5                   10                  15

Gln Arg Ala Thr Ile Ser Cys Arg Val Ser Glu Ser Ile Asp Thr Tyr
            20                  25                  30

Gly Asn Ser Phe Ile His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Ser Ala Thr Tyr Tyr Cys Gln Gln Ser Asn
                85                  90                  95

Glu Asp Pro Phe Thr Phe Gly Ser Gly Thr Lys Leu Glu Met Lys
            100                 105                 110

<210> SEQ ID NO 23
<211> LENGTH: 107
<212> TYPE: PRT
<213> ORGANISM: mus musculus

<400> SEQUENCE: 23

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Val Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Pro Pro Tyr
                85                  90                  95

Thr Phe Gly Gly Gly Thr Lys Leu Glu Ile Lys
            100                 105

```
<210> SEQ ID NO 24
<211> LENGTH: 24
<212> TYPE: DNA
<213> ORGANISM: mus musculus

<400> SEQUENCE: 24
ggatacatat tcactgcata cacc                                              24

<210> SEQ ID NO 25
<211> LENGTH: 24
<212> TYPE: DNA
<213> ORGANISM: mus musculus

<400> SEQUENCE: 25
attaaaccaa acaatggtct tgct                                              24

<210> SEQ ID NO 26
<211> LENGTH: 33
<212> TYPE: DNA
<213> ORGANISM: mus musculus

<400> SEQUENCE: 26
gcaagatctg agattacgac ggaatttgac tac                                    33

<210> SEQ ID NO 27
<211> LENGTH: 24
<212> TYPE: DNA
<213> ORGANISM: mus musculus

<400> SEQUENCE: 27
ggttattcat tcactgacta cacc                                              24

<210> SEQ ID NO 28
<211> LENGTH: 24
<212> TYPE: DNA
<213> ORGANISM: mus musculus

<400> SEQUENCE: 28
attaatcctt acaatggtgg tact                                              24

<210> SEQ ID NO 29
<211> LENGTH: 33
<212> TYPE: DNA
<213> ORGANISM: mus musculus

<400> SEQUENCE: 29
gcaagagagg aaattacgaa ggactttgat ttc                                    33

<210> SEQ ID NO 30
<211> LENGTH: 24
<212> TYPE: DNA
<213> ORGANISM: mus musculus

<400> SEQUENCE: 30
ggatacacat tcactgacta caac                                              24

<210> SEQ ID NO 31
<211> LENGTH: 24
<212> TYPE: DNA
<213> ORGANISM: mus musculus

<400> SEQUENCE: 31
attaatccta acaatggtgg tact                                              24
```

<210> SEQ ID NO 32
<211> LENGTH: 42
<212> TYPE: DNA
<213> ORGANISM: mus musculus

<400> SEQUENCE: 32
gcaagaggga ggtatgttgg ttactactat gctatggact ac        42

<210> SEQ ID NO 33
<211> LENGTH: 30
<212> TYPE: DNA
<213> ORGANISM: mus musculus

<400> SEQUENCE: 33
gaaagtgttg atagttatgc caatagtttt        30

<210> SEQ ID NO 34
<211> LENGTH: 9
<212> TYPE: DNA
<213> ORGANISM: mus musculus

<400> SEQUENCE: 34 cgtgcatcc        9

<210> SEQ ID NO 35
<211> LENGTH: 27
<212> TYPE: DNA
<213> ORGANISM: mus musculus

<400> SEQUENCE: 35
cagcaaagta aggaggatcc tctcacg        27

<210> SEQ ID NO 36
<211> LENGTH: 30
<212> TYPE: DNA
<213> ORGANISM: mus musculus

<400> SEQUENCE: 36
gaaagtattg atacttatgg caatagtttt        30

<210> SEQ ID NO 37
<211> LENGTH: 27
<212> TYPE: DNA
<213> ORGANISM: mus musculus

<400> SEQUENCE: 37
cagcaaagta atgaggatcc attcacg        27

<210> SEQ ID NO 38
<211> LENGTH: 18
<212> TYPE: DNA
<213> ORGANISM: mus musculus

<400> SEQUENCE: 38
gagaatattt acagtaat        18

<210> SEQ ID NO 39
<211> LENGTH: 9
<212> TYPE: DNA
<213> ORGANISM: mus musculus

<400> SEQUENCE: 39 gctgcaaca        9

<210> SEQ ID NO 40
<211> LENGTH: 27
<212> TYPE: DNA
<213> ORGANISM: mus musculus

<400> SEQUENCE: 40
caacattttt ggggtcctcc gtacacg                                          27

<210> SEQ ID NO 41
<211> LENGTH: 354
<212> TYPE: DNA
<213> ORGANISM: mus musculus

<400> SEQUENCE: 41
gaggtccagc tgcaacagtc tggacctgag ctggtgaagc ctggggcttc agtgaagata     60
tcctgcaaga cttctggata catattcact gcatacacca tgcactgggt gaggcagagc    120
cttggagaga gccttgactg gattggaggt attaaaccaa acaatggtct tgctaactac    180
aaccagaagt tcaagggcaa ggccacattg actgtagaca gtcctccag cacagcctac     240 atggacctcc gcagcctgac atctgaggat tctgcagtct attactgtgc aagatctgag    300
attacgacgg aatttgacta ctggggccaa ggcaccgctc tcacagtctc ctca          354

<210> SEQ ID NO 42
<211> LENGTH: 354
<212> TYPE: DNA
<213> ORGANISM: mus musculus

<400> SEQUENCE: 42
gaggtccagc tgcaacagtc tggacctgaa ctggtgaagc ctggagcttc aatgaagatt     60
tcctgcaagg cttctggtta ttcattcact gactacaccc tgaactgggt gaagcagagc    120
catggaaaga cccttgagtg gattggactt attaatcctt acaatggtgg tactacctac    180
aaccagaagt tcaagggcaa ggccacatta actgtagaca gtcatccag cacagcctac     240 atggagctcc tcagtctgac atctgaggac tctgcagtct attactgtgc aagagaggaa    300
attacgaagg actttgattt ctggggccaa ggcaccactc tcacagtctc ctca          354

<210> SEQ ID NO 43
<211> LENGTH: 363
<212> TYPE: DNA
<213> ORGANISM: mus musculus

<400> SEQUENCE: 43
gaggtcctgc tgcaacagtc tggacctgag ctggtgaagc ctggggcttc agtgaagata     60
ccctgcaagg cttctggata cacattcact gactacaaca tggactgggt gaagcagagc    120
catggaatga gccttgagtg gattggagat attaatccta acaatggtgg tactatcttc    180
aaccagaagt tcaagggcaa ggccacattg actgtagaca agtcctccag cacagcctac    240
atggagctcc gcagcctgac atctgaggac actgcagtct attactgtgc aagagggagg    300
tatgttggtt actactatgc tatggactac tggggtcaag gaacctcagt caccgtctcc    360
tca                                                                  363

<210> SEQ ID NO 44
<211> LENGTH: 333
<212> TYPE: DNA
<213> ORGANISM: mus musculus

<400> SEQUENCE: 44

```
gacattgtgc tgacccaatc tccagcttct ttggctgtgt ctctagggca gagggccacc    60
atatcctgca gagccagtga aagtgttgat agttatgcca atagttttat gcactggtac   120
cagcagaaac caggacagcc acccaaactc ctcatctatc gtgcatccaa cctagaatct   180
gggatccctg ccaggttcag tggcagtggg tctaggacag acttcaccct caccattaat   240
cctgtggagg ctgatgatgt tgcaacctat tactgtcagc aaagtaagga ggatcctctc   300
acgttcggct cggggacaaa attggaaatg aaa                                333

<210> SEQ ID NO 45
<211> LENGTH: 333
<212> TYPE: DNA
<213> ORGANISM: mus musculus

<400> SEQUENCE: 45
ggcattgtgt tgacccaatc tccagcttct ttggctgtgt ctctaggaca gagggccacc    60
atatcctgca gagtcagtga aagtattgat acttatggca atagttttat acactggtac   120
cagcagaaac caggacagcc acccaaactc ctcatctatc gtgcatccaa cctagaatct   180
gggatccctg ccaggttcag tggcagtggg tctaggacag acttcaccct caccattaat   240
cctgtggagg ctgatgattc tgcaacctat tactgtcagc aaagtaatga ggatccattc   300
acgttcggct cggggacaaa gttggaaatg aaa                                333

<210> SEQ ID NO 46
<211> LENGTH: 321
<212> TYPE: DNA
<213> ORGANISM: mus musculus

<400> SEQUENCE: 46
gacatccaga tgactcagtc tccagcctcc ctatctgtat ctgtgggaga aactgtcacc    60
atcacatgtc gagcaagtga gaatatttac agtaatttag catggtatca gcagaaacag   120
ggaaaatctc ctcagctcct ggtctatgct gcaacaaact tagtagatgg tgtgccatca   180
aggttcagtg gcagtggatc aggcacacag tattccctca agatcaacag cctgcagtct   240
gaagattttg ggagttatta ctgtcaacat ttttggggtc ctccgtacac gttcggaggg   300
gggaccaagc tggagataaa g                                              321

<210> SEQ ID NO 47
<211> LENGTH: 8
<212> TYPE: PRT
<213> ORGANISM: mus musculus

<400> SEQUENCE: 47

Gly Tyr Thr Phe Thr Ser Tyr Trp
1               5

<210> SEQ ID NO 48
<211> LENGTH: 8
<212> TYPE: PRT
<213> ORGANISM: mus musculus

<400> SEQUENCE: 48

Ile Asn Pro Thr Thr Gly Ser Thr
1               5

<210> SEQ ID NO 49
<211> LENGTH: 11
<212> TYPE: PRT
<213> ORGANISM: mus musculus
```

<400> SEQUENCE: 49

Ala Ile Gly Gly Tyr Gly Ser Trp Phe Ala Tyr
1               5                   10

<210> SEQ ID NO 50
<211> LENGTH: 7
<212> TYPE: PRT
<213> ORGANISM: mus musculus

<400> SEQUENCE: 50

Ser Ser Val Ser Ser Thr Tyr
1               5

<210> SEQ ID NO 51
<211> LENGTH: 3
<212> TYPE: PRT
<213> ORGANISM: mus musculus

<400> SEQUENCE: 51

Thr Thr Ser
1

<210> SEQ ID NO 52
<211> LENGTH: 9
<212> TYPE: PRT
<213> ORGANISM: mus musculus

<400> SEQUENCE: 52

His Gln Trp Ser Ser Tyr Pro Phe Thr
1               5

<210> SEQ ID NO 53
<211> LENGTH: 118
<212> TYPE: PRT
<213> ORGANISM: mus musculus

<400> SEQUENCE: 53

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Tyr Ile Asn Pro Thr Thr Gly Ser Thr Asp Tyr Asn Gln Lys Leu
    50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Ile Gly Gly Tyr Gly Ser Trp Phe Ala Tyr Trp Gly Gln Gly Thr
            100                 105                 110

Leu Val Thr Val Ser Ala
        115

<210> SEQ ID NO 54
<211> LENGTH: 108
<212> TYPE: PRT
<213> ORGANISM: mus musculus

<400> SEQUENCE: 54

Gln Ile Val Leu Thr Gln Ser Pro Ala Ile Met Ser Ala Ser Pro Gly

```
              1               5                  10                 15
          Glu Lys Val Thr Leu Thr Cys Ser Ala Ser Ser Ser Val Ser Ser Thr
                          20                  25                 30

Tyr Leu Tyr Trp Tyr Gln Gln Lys Pro Gly Ser Ser Pro Lys Leu Trp
                          35                  40                 45

Ile Tyr Thr Thr Ser Ile Leu Ala Ser Gly Val Pro Ala Arg Phe Ser
                   50                  55                  60

Gly Ser Gly Ser Gly Thr Ser Tyr Ser Leu Thr Ile Ser Ser Met Glu
          65                   70                  75                  80

Thr Glu Asp Ala Ala Ser Tyr Phe Cys His Gln Trp Ser Ser Tyr Pro
                           85                  90                  95

Phe Thr Phe Gly Ser Gly Thr Lys Leu Asp Ile Lys
                          100                 105
```

<210> SEQ ID NO 55
<211> LENGTH: 24
<212> TYPE: DNA
<213> ORGANISM: mus musculus

<400> SEQUENCE: 55
ggctacactt ttacttccta ctgg                                           24

<210> SEQ ID NO 56
<211> LENGTH: 24
<212> TYPE: DNA
<213> ORGANISM: mus musculus

<400> SEQUENCE: 56
attaacccta ccactggttc tact                                           24

<210> SEQ ID NO 57
<211> LENGTH: 33
<212> TYPE: DNA
<213> ORGANISM: mus musculus

<400> SEQUENCE: 57
gcaataggag gatatgggtc ctggtttgct tac                                 33

<210> SEQ ID NO 58
<211> LENGTH: 21
<212> TYPE: DNA
<213> ORGANISM: mus musculus

<400> SEQUENCE: 58
tcaagtgtaa gttccaccta c                                              21

<210> SEQ ID NO 59
<211> LENGTH: 9
<212> TYPE: DNA
<213> ORGANISM: mus musculus

<400> SEQUENCE: 59 accacatcc                                                             9

<210> SEQ ID NO 60
<211> LENGTH: 27
<212> TYPE: DNA
<213> ORGANISM: mus musculus

<400> SEQUENCE: 60
catcagtgga gtagttaccc attcacg                                        27

```
<210> SEQ ID NO 61
<211> LENGTH: 354
<212> TYPE: DNA
<213> ORGANISM: mus musculus

<400> SEQUENCE: 61
caggtccagc ttcagcagtc tggggctgaa ctggcaaaac ctggggcctc agtgaagatg      60
tcctgcaagg cttctggcta cacttttact tcctactgga tgaactgggt gaaacagagg     120
cctggacagg gtctggaatg gattggatac attaaccct ccactggttc tactgactac     180
aatcagaagt taaaggacaa ggccacattg actgcagaca atcctccaa cacagcctac     240 atgcaactga gcagcctgac atctgaggac tctgcagtct attactgtgc aataggagga     300
tatgggtcct ggtttgctta ctggggccaa gggactctgg tcactgtctc tgca           354

<210> SEQ ID NO 62
<211> LENGTH: 324
<212> TYPE: DNA
<213> ORGANISM: mus musculus

<400> SEQUENCE: 62
caaattgttc tcacccagtc tccagcaatc atgtctgcat ctcctgggga aaggtcacc      60 ttgacctgca gtgccagctc aagtgtaagt tccacctact tgtactggta ccagcagaag    120
ccaggatcct cccccaaact ctggatttat accacatcca tcctggcttc tggagtccct    180
gctcgcttca gtggcagtgg gtctgggacc tcttactctc tcacaatcag cagcatggag    240
actgaagatg ctgcctctta tttctgccat cagtggagta gttacccatt cacgttcggc    300
tcggggacaa agttggacat aaaa                                           324
```